(12) United States Patent
Olson et al.

(10) Patent No.: US 11,439,318 B2
(45) Date of Patent: Sep. 13, 2022

(54) ACTIVE MAGNETIC POSITION SENSOR

(71) Applicant: St. Jude Medical, Cardiology Division, Inc., St. Paul, MN (US)

(72) Inventors: Gregory K. Olson, Elk River, MN (US); Troy T. Tegg, Elk River, MN (US); Andrew R. Oliverius, Eagan, MN (US); Zachary L. Helgeson, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 17/092,742

(22) Filed: Nov. 9, 2020

(65) Prior Publication Data

US 2021/0052191 A1 Feb. 25, 2021

Related U.S. Application Data

(63) Continuation of application No. 15/568,637, filed as application No. PCT/US2016/035808 on Jun. 3, 2016.

(60) Provisional application No. 62/170,466, filed on Jun. 3, 2015.

(51) Int. Cl.
*A61B 18/14* (2006.01)
*A61B 5/01* (2006.01)
*A61B 5/06* (2006.01)
*A61B 5/00* (2006.01)

(52) U.S. Cl.
CPC .............. *A61B 5/062* (2013.01); *A61B 5/065* (2013.01); *A61B 5/6852* (2013.01)

(58) Field of Classification Search
CPC combination set(s) only.
See application file for complete search history.

(56) References Cited

U.S. PATENT DOCUMENTS

| | | | |
|---|---|---|---|
| 4,813,429 A * | 3/1989 | Eshel | A61B 5/01 600/549 |
| 5,644,230 A | 7/1997 | Pant et al. | |
| 5,843,076 A | 12/1998 | Webster, Jr. et al. | |
| 6,078,830 A | 6/2000 | Levin et al. | |
| 6,233,476 B1 | 5/2001 | Strommer et al. | |
| 6,278,271 B1 | 8/2001 | Schott | |
| 6,288,533 B1 | 9/2001 | Haeberli et al. | |
| 6,522,131 B1 | 2/2003 | Hiligsmann et al. | |

(Continued)

FOREIGN PATENT DOCUMENTS

| | | |
|---|---|---|
| CN | 1911159 A | 2/2007 |
| CN | 104271035 A | 1/2015 |

(Continued)

OTHER PUBLICATIONS

Author Unknown, "Triaxis: The Position Sensing Solution for your application!," webpage: http://www.melexis.com/Position-Speed-Sensors/Triaxis%C2%AE-Hall-ICs/Triaxis-760.aspx; May 11, 2015 (discovered); 2 pages [Copy provided in parent U.S. Appl. No. 15/568,637].

*Primary Examiner* — Patricia J Park
(74) *Attorney, Agent, or Firm* — Dykema Gossett PLLC

(57) ABSTRACT

An medical device, comprising an elongate shaft extending along a shaft longitudinal axis and comprising a shaft proximal portion and a shaft distal portion that is sized and configured for insertion into a body. An active magnetic position sensor can be disposed within the shaft distal portion.

16 Claims, 11 Drawing Sheets

(56) References Cited

U.S. PATENT DOCUMENTS

| | | |
|---|---|---|
| 6,545,462 B2 | 4/2003 | Schott et al. |
| 7,197,354 B2 | 3/2007 | Sobe |
| 7,386,339 B2 | 6/2008 | Strommer et al. |
| 8,187,267 B2 | 5/2012 | Pappone et al. |
| 2002/0004644 A1* | 1/2002 | Koblish ............. A61B 18/1492 604/104 |
| 2004/0077976 A1* | 4/2004 | Wilson ............. A61B 17/2202 601/2 |
| 2005/0090816 A1 | 4/2005 | McClurken et al. |
| 2008/0015570 A1 | 1/2008 | Ormsby et al. |
| 2009/0093806 A1* | 4/2009 | Govari ............. A61B 18/1492 606/34 |
| 2010/0152731 A1* | 6/2010 | de la Rama ...... A61M 25/0074 606/41 |
| 2010/0249571 A1 | 9/2010 | Jensen et al. |
| 2012/0157991 A1 | 6/2012 | Christian |
| 2013/0253504 A1 | 9/2013 | Fang |
| 2013/0296692 A1 | 11/2013 | Vanney et al. |
| 2014/0200441 A1 | 7/2014 | Potter et al. |
| 2014/0206985 A1 | 7/2014 | Kariv |
| 2014/0276748 A1* | 9/2014 | Ku ..................... A61B 18/1492 606/33 |
| 2014/0276759 A1* | 9/2014 | Kim .................. A61B 18/1492 606/33 |
| 2015/0297290 A1* | 10/2015 | Beeckler ............. A61B 18/1477 606/34 |
| 2015/0305807 A1* | 10/2015 | Kelly ................. A61B 18/1492 606/41 |
| 2015/0351832 A1 | 12/2015 | Oliverius et al. |

FOREIGN PATENT DOCUMENTS

| | | | |
|---|---|---|---|
| EP | 1743574 B1 | 3/2015 | |
| WO | WO-2013101923 A1 * | 7/2013 | ......... A61B 18/1206 |
| WO | 2014029885 A1 | 2/2014 | |

* cited by examiner

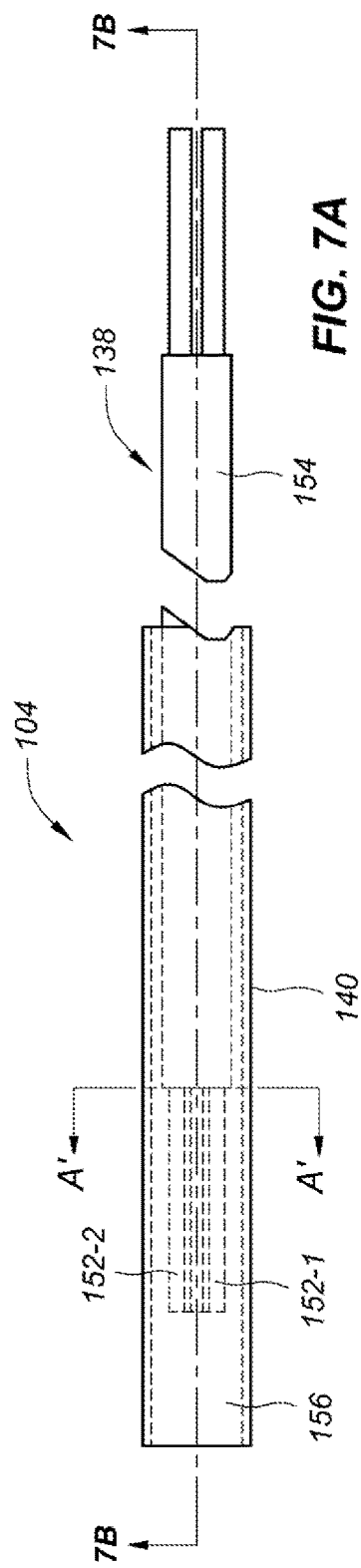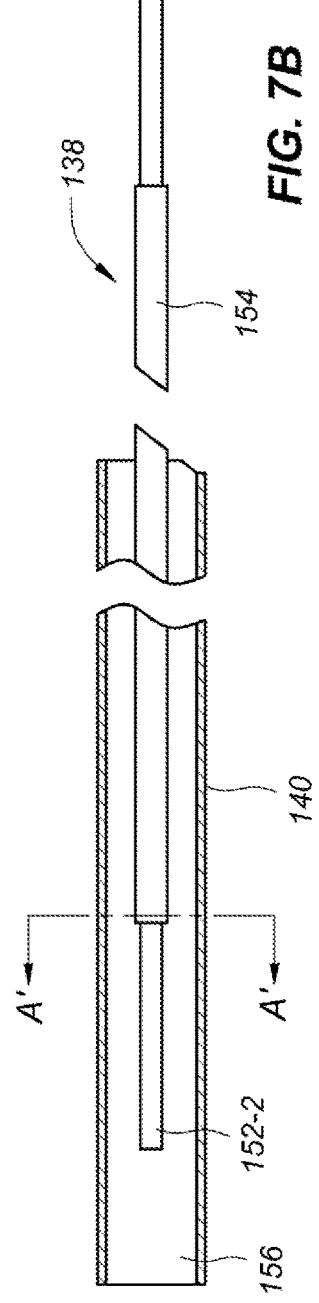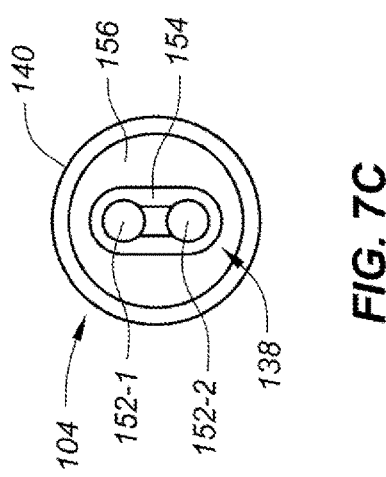

ACTIVE MAGNETIC POSITION SENSOR

CROSS-REFERENCE TO RELATED APPLICATIONS

This application is a continuation of U.S. patent application Ser. No. 15/568,637, filed on 23 Oct. 2017 (the '637 application) and published on 7 Jun. 2018 under United States patent publication no. US 2018/0153436 A1. The '637 application is a United States national stage application of international patent application no. PCT/US2016/035808, filed on 3 Jun. 2016 (the '808 application) and published in English on 8 Dec. 2016 under international publication no. WO/2016/196985, which claims priority to U.S. provisional patent application No. 62/170,466, filed on 3 Jun. 2015 (the '466 application). This application is also related to U.S. patent application Ser. No. 14/724,169, filed on 28 May 2015 (the '169 application), published on 10 Dec. 2015 under United States patent publication no. US 2015/0351832 A1, and issued on 10 Jul. 2018 as U.S. Pat. No. 10,016,234. The '637 application, the '808 application, the '466 application, and the '169 application are all hereby incorporated by reference as though fully set forth herein.

BACKGROUND a. Field

The instant disclosure relates to a medical device including a position sensor.

b. Background Art

Medical devices such as guidewires, catheters, introducers and the like that include electromagnetic coil position sensors or electrodes for device navigation are used in various medical procedures in the body. For example, it is known to equip a catheter with multiple coils sufficient to allow a position sensing system to detect six (6) degrees-of-freedom (DOF), namely, a three-dimensional (3D) position (X, Y, Z) and a 3D orientation (e.g., roll, pitch, yaw) thereof. However, the design of a coil assembly that can provide such functionality provides challenges, particularly with respect to space constraints.

One known electromagnetic position sensor includes a coil wound symmetrically on a tubular core. Such a sensor may be seen by reference to U.S. Pat. No. 7,197,354, entitled "System for Determining the Position and Orientation of a Catheter" issued to Sobe, hereby incorporated by reference in its entirety as though fully set forth herein. Sobe discloses a core that is hollow, is symmetric about a central axis, and can be scaled in length, inner diameter, and outer diameter for a particular application. A coil is wound on the core in a desired winding pattern. The coil, like the core, is symmetric about the central axis. The sensor can be used in a system to detect position in 3D space defined by three perpendicular axes (X, Y, and Z), as well as rotation about two of the three axes (e.g., pitch and yaw), but the coil cannot detect rotation about the central axis of the core (e.g., roll). Accordingly, a medical device that incorporates a single sensor coil mounted symmetric about the central axis of the medical device only senses five (5) DOF, that is, two orientation parameters, in addition to three position parameters. Despite the DOF limitation, there are nonetheless desirable aspects of the above configuration. For example, the configuration uses minimal space and accommodates an open central lumen.

Electrode mapping systems, particularly the EnSite™ Velocity™ cardiac mapping system available from St. Jude Medical, utilize an electrical field to localize a medical device within a patient's body. As is known, electrodes can be disposed in a spaced apart relationship along an axis of a catheter shaft. The electrodes can detect the electrical field generated by such a system and thereby detect position in 3D space defined by three perpendicular axes (X, Y, and Z), as well as rotation about two of the three axes (e.g., pitch and yaw), but the electrodes cannot detect rotation about the central axis of the catheter shaft (e.g., roll).

SUMMARY

Embodiments of the present disclosure can include a medical device. The medical device can include an elongate shaft extending along a shaft longitudinal axis and comprising a shaft proximal portion and a shaft distal portion that is sized and configured for insertion into a body. An active magnetic position sensor can be disposed within the shaft distal portion.

Embodiments of the present disclosure can include a medical device. The medical device can include an elongate shaft extending along a shaft longitudinal axis and comprising a shaft proximal portion and a shaft distal portion that is sized and configured for insertion into a body. An active magnetic position sensor can be disposed within the distal portion of the elongate shaft. A power source can be electrically coupled with the active magnetic position sensor.

Embodiments of the present disclosure can include a method for determining a position and orientation of a medical device. The method can include generating a signal with an active magnetic position sensor disposed within an elongate shaft of the medical device. The method can include receiving, with a computer, the generated signal from the active magnetic position sensor, wherein the received signal includes information indicative of a position and orientation of the active magnetic position sensor. The method can include determining, with the computer, the position and orientation of the medical device based on the generated signal.

In various embodiments, a catheter tip assembly can comprise a proximal stem that includes a lumen. An electrode wall that comprises a center cavity can be coupled to the distal end of the proximal stem and an electrode cap can be coupled to a distal end of the electrode wall. An elongate thermocouple can extend through the lumen of the proximal stem and the center cavity and can be coupled to the electrode cap. The elongate thermocouple can be turned around a portion of a longitudinal axis defined by the catheter tip assembly. In some embodiments, the elongate thermocouple can be turned around the portion of the longitudinal axis in a range of 0.2 and 1 turn. The elongate thermocouple can be turned around the portion of the longitudinal axis between a distal end of the proximal stem and a proximal end of the electrode cap. In some embodiments, a catheter shaft can be coupled to a proximal end of the proximal stem and the elongate thermocouple can extend from the electrode cap through a lumen of the catheter. In some embodiments, a coil can extend between the distal end of the proximal stem and the proximal end of the electrode cap and can have a spring force in a range of 15 to 100 grams. In some embodiments, a fluid lumen manifold can extend through the lumen of the proximal stem and the elongate thermocouple can be turned around a portion of the fluid lumen manifold. The elongate thermocouple can be adhered to the electrode cap and the proximal stem. In some embodiments, the elongate thermocouple can be inserted within a lumen of a formed polymer tube and a distal end of the formed polymer tube can be located within an electrode pocket in the electrode cap.

In various embodiments, a catheter can comprise a proximal stem that comprises a manifold lumen and a thermocouple lumen. An electrode wall that comprises a center cavity can be in communication with the manifold lumen and the thermocouple lumen. In some embodiments, the electrode wall can be coupled to a distal end of the proximal stem. An electrode cap can be coupled to a distal end of the electrode wall. In some embodiments, a fluid lumen manifold that can extend through the manifold lumen a defined distance into the center cavity. An elongate thermocouple can extend through the thermocouple lumen and can be coupled to the electrode cap and the elongate thermocouple can be turned around a portion of the fluid lumen manifold. In some embodiments, the elongate thermocouple can be turned around the portion of the fluid lumen manifold between a distal end of the proximal stem and a proximal end of the electrode cap. A catheter shaft can be coupled to a proximal end of the proximal stem and the elongate thermocouple can extend through the catheter shaft to a proximal end of the catheter shaft. In some embodiments, a coil can be located in the center cavity and can extend between the distal end of the proximal stem and the proximal end of the electrode cap. The coil can encircle the elongate thermocouple and the fluid lumen manifold. In some embodiments, the manifold lumen and the thermocouple lumen can be connected and in some embodiments, the manifold lumen and the thermocouple lumen can be separate.

In various embodiments, a flexible tip electrode can comprise a proximal stem that comprises a manifold lumen and a thermocouple lumen. A flexible electrode wall that comprises a center cavity and a linear gap can be coupled to the distal end of the proximal stem. An electrode cap can be coupled to a distal end of the flexible electrode wall and a fluid lumen manifold can extend through the manifold lumen a defined distance into the center cavity. In some embodiments, an elongate thermocouple element can extend through the thermocouple lumen and can be coupled to the electrode cap. The elongate thermocouple can be turned around a portion of the fluid lumen manifold in a range of 0.2 to 1 turn. A coil can be located in the center cavity that extends between the distal end of the proximal stem and a proximal end of the electrode cap and can encircle the fluid lumen manifold and the elongate thermocouple element. In some embodiments, the electrode cap can comprise an electrode pocket formed in a distal face of the electrode cap that is in communication with the center cavity and a temperature sensing component of the thermocouple element can be adhered in the electrode pocket formed in the distal face of the electrode cap. In some embodiments, the elongate thermocouple can be inserted into a polymer tube.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 7A illustrates a side view of the thermal sensor seen in FIG. 6, in accordance with embodiments of the present disclosure.

FIG. 7B illustrates a cross-sectional view of the thermal sensor seen in FIG. 7A taken in the direction of line 7B-7B, in accordance with embodiments of the present disclosure.

FIG. 7C illustrates an end view of the thermal sensor adhered within the polymer tube seen in FIG. 7A, in accordance with embodiments of the present disclosure.

DETAILED DESCRIPTION

Figure 1:
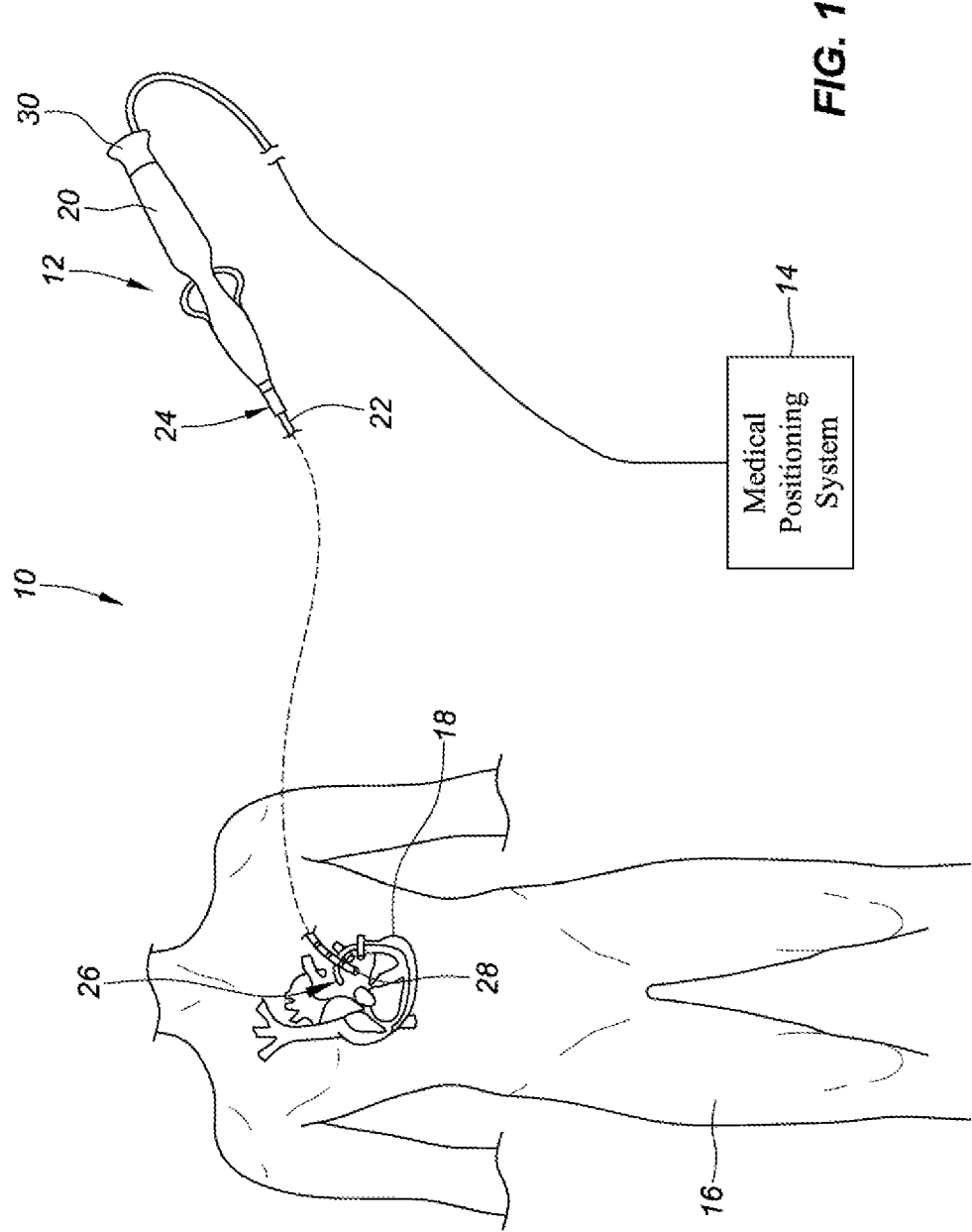
FIG. 1 depicts a diagrammatic view of an exemplary system for performing one or more diagnostic or therapeutic procedures, wherein the system comprises a magnetic field-based medical positioning system, in accordance with embodiments of the present disclosure.

In some embodiments, and with reference to FIG. 1, the system 10 can include a medical device 12 and a medical positioning system 14. The medical device 12 can include an elongate medical device such as, for example, a catheter, sheath, or a guidewire. For purposes of illustration and clarity, the description below will be limited to an embodiment wherein the medical device 12 comprises a catheter or guidewire (e.g., catheter 12', guidewire 12", 12'"). It will be appreciated, however, that the present disclosure is not meant to be limited to such an embodiment, but rather in other exemplary embodiments, the medical device may comprise other elongate medical devices, such as, for example and without limitation, sheaths, introducers, guidewires, and the like.

With continued reference to FIG. 1, the medical device 12 can be configured to be inserted into a patient's body 16, and more particularly, into the patient's heart 18. The medical device 12 may include a handle 20, a shaft 22 (e.g., elongate shaft) having a proximal end portion 24 and a distal end portion 26, and a position sensor 28 mounted in or on the shaft 22 of the medical device 12. Although one position sensor 28 is depicted in FIG. 1, embodiments of the present disclosure can include more than one position sensor 28. In an exemplary embodiment, the position sensor 28 is disposed at the distal end portion 26 of the shaft 22. The medical device 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the position sensor 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The position sensor 28 mounted in or on the shaft 22 of the medical device 12 may be provided for a variety of diagnostic and therapeutic purposes including, for example and without limitation, electrophysiological studies, pacing, cardiac mapping, and ablation. In an exemplary embodiment, the position sensor 28 can perform a location or position sensing function. More particularly, and as will be described in greater detail below, the position sensor 28 can be configured to provide information relating to the location (e.g., position and orientation) of the medical device 12, and the distal end portion 26 of the shaft 22 thereof, in particular, at certain points in time. Accordingly, in such an embodiment, as the medical device 12 is moved along a surface of a structure of interest of the heart 18 and/or about the interior of the structure, the position sensor 28 can be used to collect location data points that correspond to the surface of, and/or other locations within, the structure of interest. These location data points can then be used for a number of purposes such as, for example and without limitation, the construction of surface models of the structure of interest. For purposes of clarity and illustration, the description below will be with respect to an embodiment with a single position sensor 28. It will be appreciated, however, that in other exemplary embodiments, which remain within the spirit and scope of the present disclosure, the medical device 12 may comprise more than one position sensor 28 as well as other sensors or electrodes configured to perform other diagnostic and/or therapeutic functions. As will be described in greater detail below, the position sensor 28 can include contact leads that are configured to electrically couple the position sensor 28 to other components of the system 10, such as, for example, the medical positioning system 14.

The medical positioning system 14 can be provided for determining a position and/or orientation of the position sensor 28 of the medical device 12, and thus, the position and/or orientation of the medical device 12. In some embodiments, and in general terms, the medical positioning system 14 comprises, at least in part, an apparatus for generating a magnetic field for tracking of an object (e.g., medical device 12). The apparatus can be configured to generate low-strength magnetic field(s) in and around the patient's chest cavity in an area of interest, which can be defined as a three-dimensional space designated as area of interest. In such an embodiment, and as briefly described above, the medical device 12 includes a position sensor 28, which is a magnetic position sensor configured to detect one or more characteristics of the low-strength magnetic field(s) applied by the apparatus when the position sensor 28 is disposed within the area of interest. The position sensor 28, which in an exemplary embodiment comprises an active magnetic sensor, can be configured to generate a signal corresponding to the sensed characteristics of the magnetic field(s) to which the active magnetic sensor is exposed. The processing core can be responsive to the detected signal and can be configured to calculate a three-dimensional position and/or orientation reading for the position sensor 28. Thus, the medical positioning system 14 enables real-time tracking of each position sensor 28 of the medical device 12 in three-dimensional space, and therefore, real-time tracking of the medical device 12. In some embodiments, the medical positioning system 14 may comprise a magnetic field-based system such as, for example, the MediGuide™ system from MediGuide Ltd. (now owned by St. Jude Medical, Inc.), and as generally shown with reference to one or more of U.S. Pat. Nos. 6,233,476; 7,197,354; and 7,386,339, the entire disclosures of which are incorporated herein by reference.

Medical positioning system 14 is configured to serve as the localization system and therefore to determine position (localization) data with respect to position sensor 28 and output a respective location reading. The location readings may each include at least one or both of a position and an orientation (P&O) relative to a reference coordinate system, which may be a coordinate system of medical positioning system 14. The P&O may be expressed with six degrees-of-freedom (six DOF) as a 3D position (e.g., X, Y, Z coordinates) and 3D orientation (e.g., roll, pitch, and yaw).

The medical positioning system 14 determines respective locations (e.g., P&O) in the reference coordinate system based on capturing and processing signals received from the electromagnetic position sensor 28 while the sensor is disposed in a controlled low-strength alternating current (AC) or direct current (DC) magnetic (e.g., electromagnetic) field, for example. It should be noted that although only one position sensor 28 is shown, MPS 14 may determine P&O for multiple position sensors 28. For example, the medical device 12 discussed herein can include a plurality of active magnetic position sensors, which can provide for a plurality of positional points associated with the medical device 12.

Figure 2A:
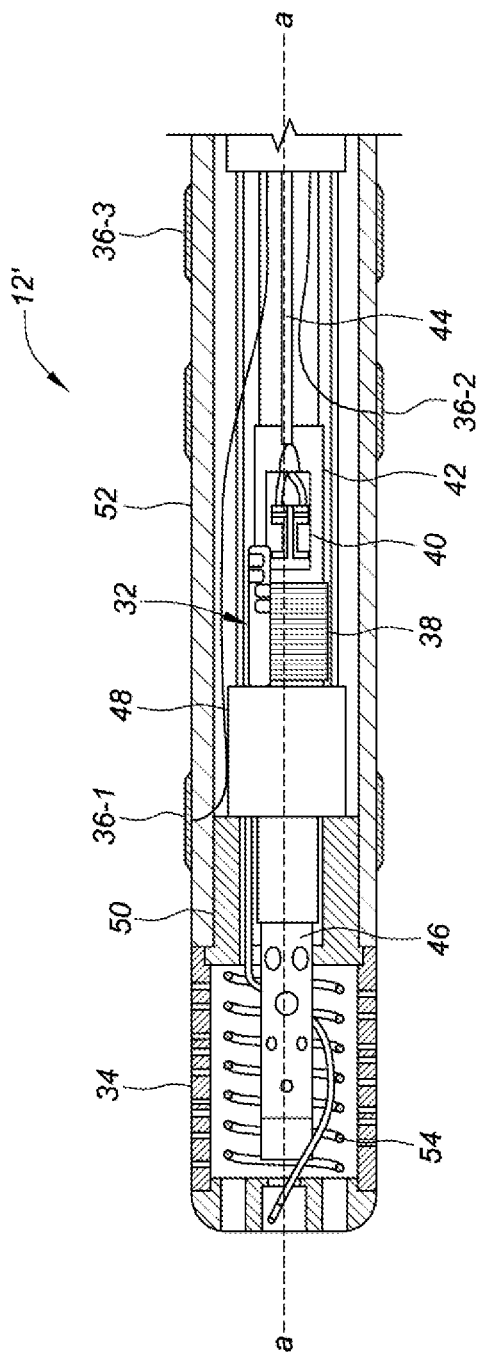
FIG. 2A depicts a cross-sectional side view of a distal portion of a catheter with an active magnetic position sensor, in accordance with embodiments of the present disclosure.

FIG. 2A depicts a cross-sectional side view of a distal portion of a catheter 12' with an active magnetic position sensor 32, in accordance with embodiments of the present disclosure. In various embodiments, the catheter 12' can include a flexible tip assembly 34, which can include, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2, United States patent application publication no. US 2010/0152731 A1, U.S. patent application Ser. No. 14/724,169, and U.S. patent application Ser. No. 14/213,289, each of which is hereby incorporated by reference as though fully set forth herein. However, in some embodiments, the catheter 12' can include other types of tip assemblies. The flexible tip assembly 34 can be connected to a proximal stem 50, which is connected to an elongate catheter shaft 52. A coil 54 can be disposed in the flexible tip assembly 34. The coil 54 can bias the flexible tip assembly 34 in a longitudinal direction or in a pre-bent configuration. Additionally, a fluid lumen manifold 46 can extend through the elongate catheter shaft 52 into the flexible tip assembly 34.

In some embodiments, the active magnetic position sensor 32 can be an active device and can require power to function and generate a P&O signal. For example, the active magnetic position sensor 32 can include an integrated circuit that needs an amount of power to function. For example, the active magnetic position sensor 32 can include an application specific integrated circuit (ASIC). In contrast, a passive magnetic position sensor (e.g., an electromagnetic coil position sensor) can be placed in a magnetic field and can generate a P&O signal that is directly induced in the coil by the magnetic field, which can be received by the medical positioning system 14. In some embodiments, the active magnetic position sensor 32 can be a software defined magnetic sensor, such as a Triaxis® sensor produced by Melexis. The active magnetic position sensor 32 can operate in a magnetic field with a magnetic field strength in a range from 20 micro Tesslas (μT) to 120 μT. In some embodiments, the active magnetic position sensor 32 can operate in a magnetic field with a magnetic field strength in a range from 1 μT to 70 μT. In an example, the magnetic position sensor 32 can operate in a magnetic field with a magnetic field strength in a range from 1 μT to 20 μT and a frequency in a range from 3 to 15 kilohertz. However, the active magnetic position sensor 32 can operate in a magnetic field with a magnetic field strength that is greater than 120 μT or less than 1 μT, depending on the type of active magnetic position sensor 32 that is used. For example, some active magnetic position sensors 32 can operate in a magnetic field with a magnetic field strength of 1 milli Tessla (mT) or higher. The active magnetic position sensor 32 can produce a signal indicative of a P&O of the medical device 12. The signal indicative of the P&O of the medical device can be generated in response to detection of the magnetic field by the active magnetic position sensor. The active magnetic position sensor 32 can require power to produce the signal indicative of the P&O of the medical device, in contrast to a passive magnetic sensor.

In some embodiments, the active magnetic position sensor 32 can include a particular material that has particular magnetoresistive properties. Such a material can be placed in various geometries with respect to the active magnetic position sensor 32. The particular material can have differing magnetoresistive properties that react differently with magnetic fields. In some embodiments, reactions between the magnetoresistive properties and the magnetic fields can be measured directly. The measured reactions between the magnetoresistive properties and the magnetic field can provide an output that can be used to calculate a P&O of the active magnetic position sensor 32 in space, and thus a P&O of the catheter 12' in space. As discussed, in some embodiments, the particular material can be arranged in a particular physical configuration with respect to the active magnetic position sensor 32. Accordingly, the particular material can provide an output that is unique to the particular physical configuration. This output can be used to calculate the P&O of the active magnetic position sensor 32.

In some embodiments, the particular material included in the active magnetic position sensor 32 can include, various types of Hall effect materials, anisotropic magnetoresistance (AMR) materials, tunnel magnetoresistance (TMR) materials, giant magnetoresistance (GMR) materials, colossal magnetoresistance (CMR) materials, or extraordinary magnetoresistance (EMR) materials. Magnetoresistance can be defined as a property of a material to change the value of its electrical resistance when an external magnetic field is applied to the material. A principal of operation that can be used in the determination of a P&O of Hall effect magnetoresistance materials can be an orbital effect, which is unrelated to a spin, due to a Lorentz force. Hall effect materials can be associated with an asymmetric distribution of charge density. A principal of operation that can be used in the determination of a P&O of AMR materials can be associated with a transverse AMR-planar effect spin-orbit interaction, which can have a negative magnetoresistance in ferromagnets. Alternatively, a principal of operation that can be used in the determination of a P&O of AMR materials can be a Shubnikov-de Haas effect (SdH), which can have a positive magnetoresistance in metals. A principal of operation that can be used in the determination of a P&O of TMR materials can be associated with electron tunneling between two ferromagnets between which is disposed a thin insulator. A magnetic field in which the ferromagnets are present can be turned on and off in the determination of the P&O of TMR materials. A principal of operation that can be used in the determination of a P&O of GMR material can be associated with electron scattering on spin orientation. The GMR material can include adjacent magnetized ferromagnetic layers. A principal of operation that can be used in the determination of a P&O of CMR materials can include spin orientation, where a conductivity of the CMR material changes as a magnetic field is aligned with an electron spin associated with the CMR material. A principal of operation that can be used in the determination of a P&O of EMR materials can be associated with the Hall effect.

In some embodiments, the active magnetic position sensor 32 can be used to determine a P&O of the catheter 12'. For example, the active magnetic position sensor 32 can determine the P&O of the catheter 12' with six DOF. In some embodiments, the determination of the P&O of the catheter 12' with six DOF can be used as an input for a force vector determination with respect to the catheter 12'. In some embodiments, the active magnetic position sensor 32 can determine the P&O of the catheter 12' with fewer than six DOF. For example, the P&O of the catheter 12' can be determined with five degrees of freedom.

In some embodiments, the active magnetic position sensor 32 can be disposed within the catheter 12'. In an example, the active magnetic position sensor 32 can be disposed along a longitudinal axis aa of the catheter 12'. In some embodiments, the active magnetic position sensor 32 can be coaxial with the longitudinal axis aa. In some embodiments, the active magnetic position sensor 32 can be disposed off-axis with respect to the longitudinal axis aa. For example, an elongate axis of the active magnetic position sensor 32 can be parallel with the longitudinal axis aa and/or can be divergent with the longitudinal axis aa. In some embodiments, the active magnetic position sensor 32 can be disposed in a same place where a passive magnetic position sensor (e.g., an electromagnetic coil position sensor) would be placed. For example, the active magnetic position sensor 32 can be disposed in a same place as magnetic coil assembly 38. As previously discussed, the magnetic coil assembly 38 may not be included in the catheter 12', since a P&O of the catheter 12' can be determined instead through the active magnetic position sensor 32.

For illustrative purposes, the catheter 12' is shown with ring electrodes 36-1, 36-2, 36-3 and a magnetic coil assembly 38. The magnetic coil assembly 38 is depicted as connected to a printed circuit board 40 via a pair of interconnects. The printed circuit board 40 is mounted on a mounting surface 42. A twisted pair 44 can connect the magnetic coil assembly 38 to the medical positioning system 14. In some embodiments of the present disclosure, the ring electrodes 36-1, 36-2, 36-3 and the magnetic coil assembly 38 are not needed, as the P&O of the catheter 12' can be detected via the active magnetic position sensor 32. For example, the active magnetic position senor can be the only position sensor included in the catheter 12'.

Figure 2B:
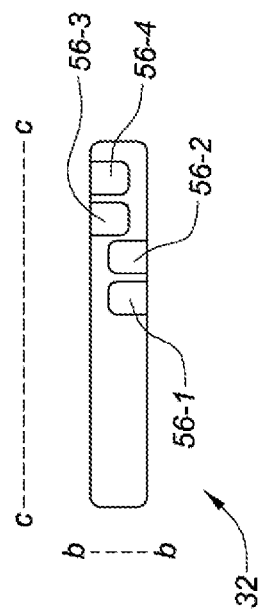
FIG. 2B depicts a side view of an active magnetic position sensor, in accordance with embodiments of the present disclosure.

As depicted in FIG. 2B, the active magnetic position sensor 32 can be disposed next to the irrigation tube 46 and proximally with respect to the stop tube 48. In some embodiments, the active magnetic position sensor 32 can be disposed within the stop tube 48 or within the proximal stem 50 that is connected to the flexible tip assembly 34. In an example, a mounting feature such as a groove or hole can be included in the stop tube 48 or the proximal stem 50 and the active magnetic position sensor 32 can be inserted into the hole. However, in some embodiments, the active magnetic position sensor 32 can be disposed within the catheter 12' at other locations.

Embodiments of the present disclosure can provide an active magnetic position sensor 32 that provides the P&O of the catheter 12' with six DOF using a single sensor. In contrast, many single coil sensors used in prior approaches can be limited to five DOF. In addition, the active magnetic position sensor 32 can have a form factor that can allow the active magnetic position sensor 32 to be placed in a wide variety of devices, due to its small size. Further, the active magnetic position sensor 32 can provide for savings related to a cost of goods associated with use of the active magnetic position sensor 32 and a cost of labor associated with constructing and installing the active magnetic position sensor 32.

FIG. 2B depicts a side view of an active magnetic position sensor 32, in accordance with embodiments of the present disclosure. In some embodiments, the active magnetic position sensor 32 can be elongated and sized to fit within a catheter. In contrast to present active magnetic position sensors, the active magnetic position sensor 32 can be smaller to enable it to fit within a catheter. In some embodiments, the active position sensor 32 can have an outside diameter defined by line bb, in a range from 0.001 inches to 0.015 inches. In some embodiments, the outside diameter of the active magnetic position sensor 32 can be in a range from 0.003 inches to 0.01 inches. However, in some embodiments, the outside diameter of the active magnetic position sensor 32 can be less than 0.001 inches or greater than 0.015 inches. In some embodiments, a length of the active magnetic position sensor 32 defined by line cc can be in a range from 0.03 inches to 0.2 inches. In some embodiments, the length of the active magnetic position sensor 32 can be in a range from 0.05 inches to 0.1 inches. However, in some embodiments, the length of the active magnetic position senor 32 can be less than 0.03 inches or greater than 0.2 inches. In some embodiments, the active magnetic position sensor 32 can be in the shape of a rectangular block or a cylinder, among other shapes.

The active magnetic position sensor 32 can include contact pads 56-1, 56-2, 56-3, 56-4. Hereinafter, the contact pads 56-1, 56-2, 56-3, 56-4 are collectively referred to as contact pads 56. The contact pads 56 can provide connection points (e.g., inputs and outputs) for power and/or communication with the active magnetic position sensor 32 (e.g., with the medical positioning system 14). Although four contact pads 56 are depicted, the active magnetic position sensor can include fewer than four contact pads or greater than four contacts pads. In some embodiments, the active magnetic position sensor 32 can be a quad flat no-lead sensor and can be connected to a printed circuit board via the contact pads 56. For example, the active magnetic position sensor 32 can be connected via a pair of interconnects to a printed circuit board, such as printed circuit board 40 depicted in FIG. 2A, and/or the medical positioning system 14.

In some embodiments, the contact pads 56 can provide for an input and output from the active magnetic position sensor 32. For example, an input power can be provided to and/or communication can be established with the active magnetic position sensor 32 via the contact pads 56, enabling receipt of a signal produced by the active magnetic position sensor 32. Power can be provided to the active magnetic position sensor 32 via a power source that is electrically coupled to one or more of the contact pads 56. In an example, one or more electrical leads can extend through the elongate catheter shaft 52 to the active magnetic position sensor 32. In some embodiments, a power generating integrated circuit (e.g., power source) can be disposed in the catheter 12' and/or within a magnetic field generated by the medical positioning system 14. The power generating integrated circuit can pick up the magnetic field and generate a voltage/current, which can be provided to the magnetic position sensor 32. In some embodiments, the power generating integrated circuit can be included in the active magnetic position sensor, disposed in close proximity to the active magnetic position sensor 32 (e.g., in a shaft distal portion) or in another portion of the elongate catheter shaft 52 (e.g., shaft proximal portion) that is positioned within the magnetic field produced by the medical positioning system. In some embodiments, the power generating integrated circuit can be positioned within the magnetic field produced by the medical positioning system, but outside of the elongate catheter shaft 52. Power can be provided to the active magnetic position sensor 32 via contact pads 56, in some embodiments. In some embodiments, a first contact pad 56-1 can serve as an electrical ground and a second contact pad 56-2 can be a power connect.

In some embodiments, the contact pads 56 can provide for an output from the active magnetic position sensor 32. In some embodiments, signal processing can be performed on the output from the active magnetic position sensor 32 by a signal processor. The signal processor can perform filtering and/or amplification of the signal produced by the active magnetic position sensor and can be electrically coupled to one or more of the contact pads (e.g., third contact pad 56-3, fourth contact pad 56-4). In some embodiments, the signal processor can be disposed in the catheter 12'. In some embodiments, the signal processor can be included in the active magnetic position sensor, disposed in close proximity to the active magnetic position sensor 32 (e.g., in a shaft distal portion) or in another portion of the elongate catheter shaft 52 (e.g., shaft proximal portion). In some embodiments, the signal processor can be disposed outside of the elongate catheter shaft 52 (e.g., in the magnetic positioning system 14 or elsewhere). Positioning the signal processor in close proximity to the active magnetic position sensor 32 can reduce signal noise that can develop in electrical leads that connect the active magnetic position sensor 32 and the signal processor. As a length of the electrical leads that connect the active magnetic position sensor 32 and the signal processor increase the signal passing through the leads can pick up signal noise. Accordingly, by positioning the signal processor in close proximity to the active magnetic position sensor 32, the signal can be less affected by signal noise.

As depicted in FIG. 2B, a first set of contact pads, including a first contact pad 56-1 and second contact pad 56-2 are longitudinally aligned and disposed on a first side of the active magnetic position sensor 32. A second set of contact pads, including a third contact pad 56-3 and a fourth contact pad 56-4 can be longitudinally aligned and disposed on a second side of the active magnetic position sensor 32. In some embodiments, the first set of contact pads 56-1, 56-2 can be longitudinally staggered and diametrically opposed to the second set of contact pads 56-3, 56-4. The first set of contact pads 56-1, 56-2 and the second set of contact pads 56-3, 56-4 can be disposed on a proximal half of the active magnetic position sensor 32. By doing so, less wiring can be used to electrically couple the contact pads 56 of the active magnetic position sensor 32 to the magnetic positioning system 14, which can reduce a bulk associated with internal components of the catheter 12'.

Figure 3:
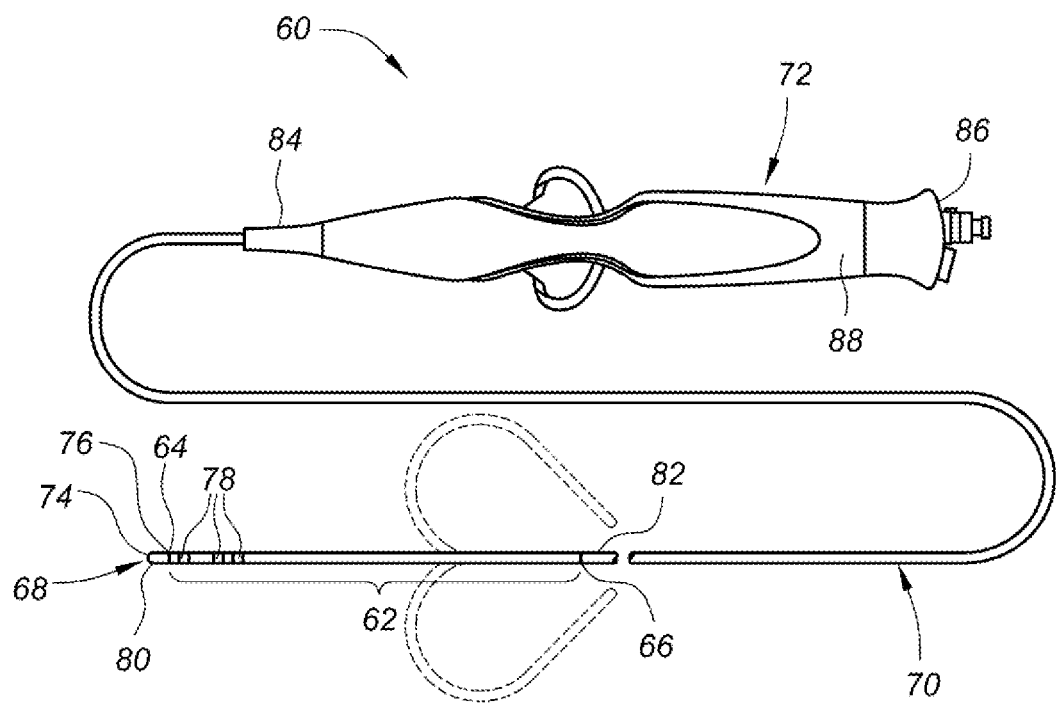
FIG. 3 illustrates a deflectable electrophysiology catheter that comprises a deflectable catheter shaft section, in accordance with embodiments of the present disclosure.

FIG. 3 illustrates a deflectable electrophysiology catheter that comprises a deflectable catheter shaft section in accordance with embodiments of the present disclosure. Deflectable catheter shaft section 62 includes an elongated body having a distal end 64 and a proximal end 66. In its most general form, catheter 60 further includes a tip assembly 68 located at the distal end 64 of the deflectable catheter shaft section 62, a proximal catheter shaft section 70 located at the proximal end 66 of the deflectable catheter shaft section 62, and a handle assembly 72. Catheter 60 may be used in any number of diagnostic and/or therapeutic applications, such as the recording of electrograms in the heart, the performance of a cardiac ablation procedure, and other similar applications/procedures. Accordingly, one of ordinary skill in the art will recognize and appreciate that the inventive deflectable catheter shaft section and method of manufacturing the same can be used in any number of diagnostic and therapeutic applications.

The deflectable catheter shaft section 62 is disposed between the tip assembly 68 and the proximal catheter shaft section 70 and can include a plurality of ring electrodes 78. The length and diameter of the deflectable catheter shaft section 62 can vary according to the application. Generally, the length of the deflectable catheter shaft section 62 can range from about 2 inches (18.8 mm) to about 6 inches (119.4 mm) and the diameter of the deflectable catheter shaft section 62 can range from about 5 French to about 12 French. The diameter of the deflectable catheter shaft section 62 can be about 7 French in accordance with some embodiments. Although these particular dimensions are mentioned in particular, the dimensions of the deflectable catheter shaft section 62 can vary in accordance with various applications of the deflectable catheter shaft section 62. The deflectable catheter shaft section 62 can be configured for deflection independent of the proximal catheter shaft section 70.

The tip assembly 68 comprises a tip electrode 80 having a distal end 74 and a proximal end 76. Tip electrode 80 may be configured for various functions and may include, without limitation, an active outer surface that is configured for exposure to blood and/or tissue. The tip electrode 80 may be affixed to distal end 64 of the deflectable catheter shaft section 62 in a number of ways. For instance, the tip electrode 80 may be bonded to an inner radial surface of the deflectable catheter shaft section 62 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 80 of the tip assembly 68 may have a recess formed therein that is sufficiently sized and configured to receive a wire that is connected to the tip electrode 80, as discussed herein. One end of the wire can be connected to the tip electrode 80 and the other end can be connected to, for example, monitoring or recording or ablation devices, such as a radiofrequency (RF) generator. The wire can be a pre-coated wire that is insulated from other components in the tip assembly 68. The tip electrode 80 of the tip assembly 68 may further include a lumen formed therein that is configured to receive a thermal sensor, as discussed herein. The thermal sensor may be configured to measure the temperature of the tip electrode 80, targeted tissue, and/or the interface therebetween and provide feedback to the monitoring or recording or ablation devices described hereinabove. The tip electrode 80 may further include a fluid lumen manifold configured as a passageway for irrigation fluid.

The proximal catheter shaft section 70 can also include one or more lumens. The proximal catheter shaft section 70 can be constructed of a series of polymer layer(s) and braid structure(s). In particular, one or more wires wound to form a cylindrical braid structure can substantially surround the one or more lumens of proximal catheter shaft section 70. In addition, a polymeric material, such as polyurethane, nylon, or various types of plastic materials such as polyether block amides offered under the trademark PEBAX®, or any other suitable material, can also substantially surround the one or more lumens of proximal catheter shaft section 70. The material can have the capability to be displaced and/or to shrink when subjected to a process, such as for example, a heating process that is performed. The mechanical properties of the proximal catheter shaft section 70 can also be varied by varying the properties of the cylindrical braid structure(s) and the polymeric material (e.g., dimension of the cylindrical braid structure and/or durometers of the polymers). Additionally, the mechanical properties of the proximal catheter shaft section 70, can be varied along the length of the proximal catheter shaft section 70 in accordance with some embodiments of the disclosure. Alternatively, the mechanical properties of the proximal catheter shaft section 70 can be substantially constant along the entire length of the proximal catheter shaft section 70, in accordance with some embodiments of the disclosure.

The handle assembly 72 can be coupled to the proximal catheter shaft section 70 at its proximal end (disposed within handle assembly 72 and not shown). The handle assembly 72 can be operative to, among other things, effect movement (i.e., deflection) of the deflectable catheter shaft section 62. The handle assembly 72 includes a distal end 84 and a proximal end 86. The handle assembly 72 includes an actuator that can be selectively manipulated to cause deflectable catheter shaft section 62 to deflect in one or more directions (e.g., up, down, left, and right). Deflectable catheter shaft section 62 may be configured for uni-directional deflection in accordance with some embodiments and may be configured for bi-directional deflection in accordance with other embodiments.

The catheter 60 may include any number of other elements such as, for example and without limitation, thermocouples, thermistor temperature sensors, etc. for monitoring the temperature of targeted tissue and controlling the temperature. In some embodiments, the catheter 60 can include a sensor for producing signals indicative of catheter location information, and may include one or more electrodes. In an example, the catheter 60 may include ring electrodes 78 that collectively define the sensor. The one or more electrodes may be provided on a distal end 64 of the catheter 60 and a localization system (e.g., EnSite™ Velocity™ system) may compute a distal location of the catheter 60 using received location information from the one or more electrodes and/or a geometrical relationship between the one or more electrodes.

Figure 4A:
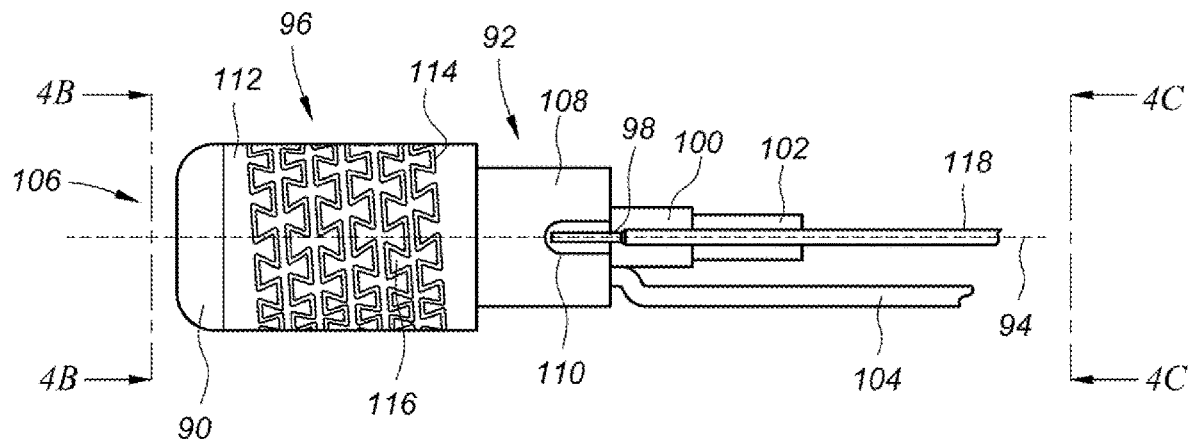
FIG. 4A illustrates a flexible tip assembly, in accordance with embodiments of the present disclosure.

In various embodiments, the catheter 60 can include a flexible tip assembly, which can include, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2 and United States patent application publication no. US 2010/0152731 A1, each of which is hereby incorporated by reference as though fully set forth herein. One embodiment of a flexible tip assembly 92 is illustrated in FIG. 4A. The flexible tip assembly 92 has a longitudinal axis 94 and can comprise a flexible tip electrode 96, an electrode wire 98, a stop tube 100, a fluid lumen manifold 102, and a thermal sensor 104. The flexible tip electrode 96 can comprise a tip electrode distal end 106, a proximal stem 108, a recess 110, and an electrode wall 112. The electrode wall 112 can be formed of a radial surface and can include at least one linear gap 114. The at least one linear gap 114 can extend along an outer radial surface of the flexible tip electrode 96 and can form a variety of patterns on the outer radial surface of the flexible tip electrode 96, allowing for the flexible tip electrode 96 to flex and/or deform to some degree when a force is exerted on a tip of the flexible tip electrode 96, for example. In one embodiment, the pattern is an interlocking dovetail pattern. The interlocking dovetail pattern can comprise a plurality of blocks 116 wherein each of the blocks comprises a head 130 and a neck 132 (see FIG. 5). Alternatively, in some embodiments, the pattern can be any type of interlocking arrangement that provides for relative movement in the proximal and distal direction with regard to either all or part of flexible tip assembly 92. For example, alternative patterns of the interlocking arrangement can be bulbous, trapezoidal, triangular, rectangular, and any other shape that creates an interlocking fit.

The electrode wire 98 can be coupled to the recess 110 of the flexible tip electrode 96. The electrode wire 98 can be coupled to the flexible tip electrode 96 by soldering, adhesive, or other methods known in the art. The electrode wire 98 can be surrounded along part of its length by a wire coating 118. The wire coating 118 can electrically insulate the electrode wire 98 from other components of the catheter. The electrode wire 98 can be connected to, for example, monitoring or recording or ablation devices, such as a radiofrequency (RF) generator.

The electrode distal end 106 can include an electrode cap 90, which can be coupled to a distal end of the electrode wall 112. The thermal sensor 104 can be positioned within an opening that passes from the distal end of the electrode cap 90 to the proximal end of the electrode cap 90 and can be used to monitor the operating temperature of the flexible tip electrode 96 or the temperature of tissue adjacent the flexible tip electrode 96. The fluid lumen manifold 102 can extend through the manifold lumen a defined distance into the center cavity. The stop tube 100 may be coupled to the fluid lumen manifold 102 and configured to interact with a portion of the flexible tip electrode 96 to control the distance that a distal end of the fluid lumen manifold 102 can extend into the flexible tip electrode 96.

Figure 4B:
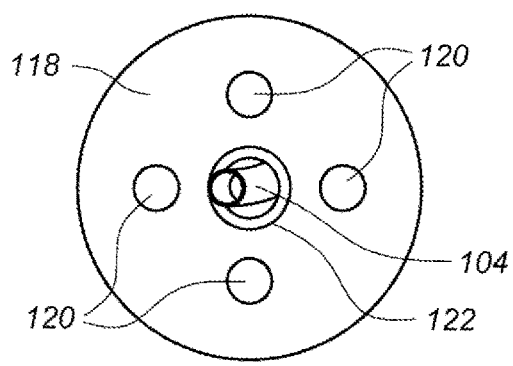
FIG. 4B illustrates an end view taken in the direction of line 4B-4B of FIG. 4A, in accordance with embodiments of the present disclosure.

FIG. 4B illustrates an end view taken in the direction of line 4B-4B of FIG. 4A, in accordance with embodiments of the present disclosure. In some embodiments, the electrode cap includes a plurality of irrigation ports 120 that pass through the electrode cap 90. The electrode cap 90 includes an electrode pocket 122, that can be configured to receive a distal end of the thermal sensor 104. As illustrated in FIG. 4B, the distal end of the thermal sensor 104 can be seen protruding into the electrode pocket 122. In some embodiments, the thermal sensor 104 can be adhered within the electrode pocket 122 in the electrode cap 90.

Figure 4C:
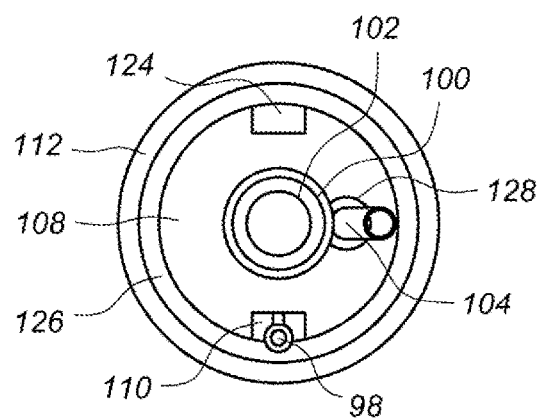
FIG. 4C illustrates an end view taken in the direction of line 4C-4C of FIG. 4A, in accordance with embodiments of the present disclosure.
Figure 6:
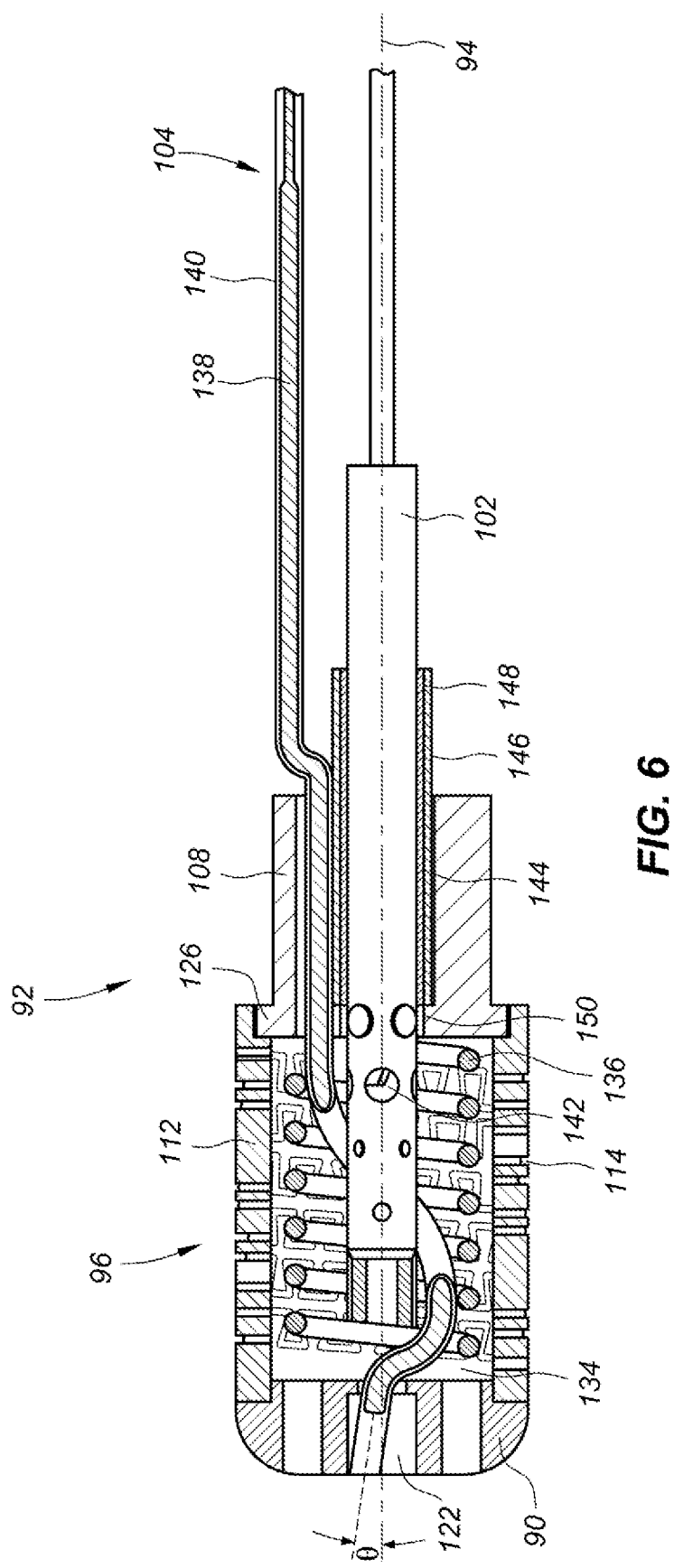
FIG. 6 illustrates a cross-sectional view of the embodiment seen in FIG. 5 taken along line 5-5, in accordance with embodiments of the present disclosure.

FIG. 4C illustrates an end view taken in the direction of line 4C-4C of FIG. 4A, in accordance with embodiments of the present disclosure. In some embodiments, the electrode wall 112 can be coupled to the proximal stem 108 via a mounting lip 126, which can be formed around a perimeter of the proximal stem 108, at the distal end of the proximal stem 108 (as shown in FIG. 6). The proximal end of the proximal stem 108 can be coupled to the proximal catheter shaft section 70. In an example, a portion of the outer surface of the proximal stem 108 can be adhered to an inner surface of the proximal catheter shaft section 70.

The proximal stem 108 can include one or more recesses 110 sized and configured to receive the electrode wire 98, which can be soldered to a distal end of the recess 110, in some embodiments. The proximal stem 108 can include a lumen through which the stop tube 100 passes and the stop tube 100 can include a lumen through which the fluid lumen manifold 102 passes. In addition, the proximal stem 108 can include a thermocouple lumen 128 through which the thermal sensor 104 can pass. In some embodiments, the thermal sensor 104 can be an elongate thermocouple and can pass from a proximal end of the proximal catheter shaft section 70, through a lumen of the proximal catheter shaft section 70, the thermocouple lumen 128 of the proximal stem 108, a center cavity of the electrode wall 112, and can be adhered within the electrode pocket 122 of the electrode cap 90.

Figure 5:
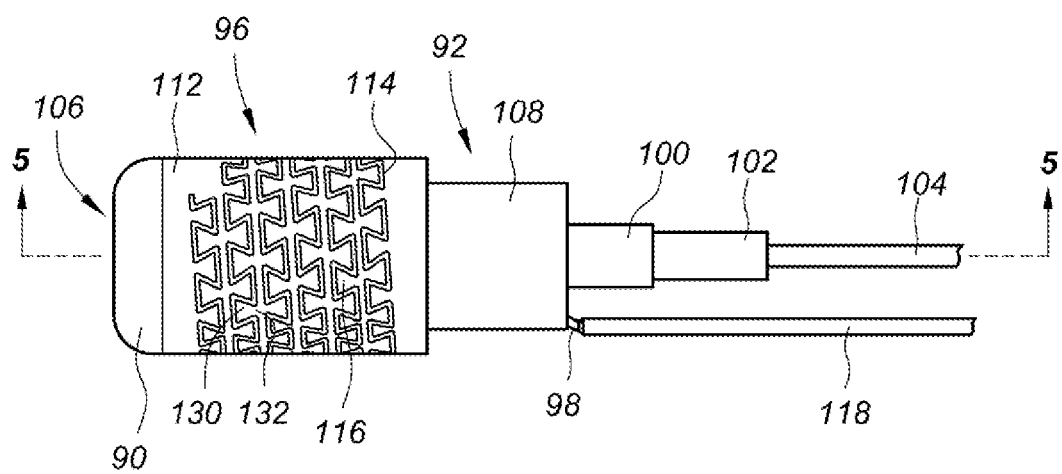
FIG. 5 illustrates the flexible tip assembly seen in FIG. 4A rotated 90 degrees about a longitudinal axis of the flexible tip assembly, in accordance with embodiments of the present disclosure.

FIG. 5 illustrates the flexible tip assembly shown in FIG. 4A rotated 90 degrees about a longitudinal axis of the flexible tip assembly, in accordance with embodiments of the present disclosure. The electrode wire 98 and the wire coating 118 covering a portion of the electrode wire 98 is illustrated traveling parallel to a longitudinal axis of the flexible tip assembly 92. The wiring of thermal sensor 104 is illustrated traveling parallel to the longitudinal axis of the flexible tip assembly 92 through the proximal stem 108 and the electrode wall 112, to the electrode cap 90. In the illustrated configuration, the wiring of the thermal sensor 104 is offset from the electrical wire 118 by 90 degrees around the outer radial surface of the flexible tip electrode 96.

The electrode wall 112 can include at least one linear gap 114. The at least one linear gap 114 can extend along an outer radial surface of the flexible tip electrode 96 and can form a variety of patterns on the outer radial surface of the flexible tip electrode 96. In one embodiment, the pattern can be an interlocking dovetail pattern. The interlocking dovetail pattern can include a plurality of blocks 116 wherein each of the blocks includes a head 130 and a neck 132. Alternatively, as discussed herein, the pattern can be any type of interlocking arrangement that provides for relative movement in the proximal and distal direction with regard to either all or part of tip assembly 68.

The electrode wire 98, surrounded by wire coating 118, is coupled to the recess of the flexible tip electrode 96. As discussed herein, the distal end of thermal sensor 104 can be adhered within the electrode pocket of the electrode cap and can be used to monitor the operating temperature of the flexible tip electrode 96 and/or the temperature of tissue adjacent the flexible tip electrode 96. The stop tube 100 may be coupled to the fluid lumen manifold 102 and configured to interact with a portion of the flexible tip electrode 96 to control the distance that a distal end of the fluid lumen manifold 102 can extend into the flexible tip electrode 96.

FIG. 6 illustrates a cross-sectional view of the embodiment illustrated in FIG. 5 taken along line 5-5, in accordance with embodiments of the present disclosure. The flexible tip electrode 96 can include a center cavity 134, a coil 136, an electrode wall 112, at least one linear gap 114, the proximal stem 108 with mounting lip 126, and the thermal sensor 104. The thermal sensor 104 can pass through the thermocouple lumen 128 of the proximal stem 108 and through the center cavity 134 in the electrode wall 112 and the distal end of the thermal sensor 104 can be adhered in the electrode pocket 122. The center cavity 134 can be in communication with the electrode pocket 122 and can also be in communication with the thermocouple lumen 128 and manifold lumen of the proximal stem 108. In some examples, the thermocouple lumen 128 and the manifold lumen can be connected and form a single lumen. Alternatively, the thermocouple lumen 128 and the manifold lumen can be separated (e.g., by a portion of the proximal stem 108) and form separate lumens.

In some embodiments, the thermal sensor 104 can be turned or wrapped around a portion of a longitudinal axis 94, defined by the catheter tip assembly 92. In an example, at least one linear gap 114 can allow the flexible tip electrode 96 to compress longitudinally along the longitudinal axis 94 defined by the catheter tip assembly 92 and/or move laterally and/or angularly with respect to the longitudinal axis 94. The thermal sensor 104 can be adhered within the thermocouple lumen 128 of the proximal stem 108 and within the electrode pocket 122. As such, when the flexible tip electrode 96 flexes, the portion of the thermal sensor 104 passing through the center cavity 134 of the flexible tip electrode 96 can flex.

In some prior approaches, the portion of the thermal sensor 104 passing through the center cavity 134 runs linearly from the proximal stem 108 to the electrode pocket 122 (e.g., parallel to the longitudinal axis 94). In an example, the thermal sensor 104 passes through the center cavity 134 linearly (e.g., without a bend in the thermal sensor 104). a result, a stress point can occur where the thermal sensor 104 exits the thermocouple lumen 128 of the proximal stem 108 and enters the center cavity 134. In addition, a stress point can occur where the thermal sensor 104 enters the electrode pocket 122 from the center cavity 134. In some examples, because the thermal sensor 104 is run linearly from the proximal stem 108 to the electrode pocket 122, minimal slack is present in the thermal sensor 104, which can cause the thermal sensor 104 to bend and create stress points where the thermal sensor 104 exits the thermocouple lumen 128 of the proximal stem 108 and enters the center cavity 134 and where the thermal sensor 104 enters the electrode pocket 122 from the center cavity 134. For example, the thermal sensor 104 can bend as a result of the longitudinal compression and/or lateral and/or angular movement of the flexible tip electrode 96. Other prior approaches have placed a thermal sensor in the proximal stem 108 to reduce stress exerted on the thermal sensor 104. However, placing the thermal sensor 104 in the proximal stem 108 can result in an inaccurate temperature reading of the flexible tip electrode 96 and/or tissue adjacent the flexible tip electrode 96, because of a lack of proximity to those areas.

Accordingly, embodiments of the present disclosure can include routing the thermal sensor 104 through the center cavity 134 in a way that avoids causing stress points, for example, where the thermal sensor 104 exits the thermocouple lumen 128 of the proximal stem 108 and enters the center cavity 134 and where the thermal sensor 104 enters the electrode pocket 122 from the center cavity 134. In some embodiments, the thermal sensor 104 is turned or wrapped at least partially around a portion of the longitudinal axis 94 defined by the catheter tip assembly 92. In an example, the thermal sensor 104 can be turned or wrapped around the portion of the longitudinal axis 94 between the distal end of the proximal stem 108 and the proximal end of the electrode cap 90. The thermal sensor 104 may, for example, be turned or wrapped around the portion of the longitudinal axis 94 in a range of 0.2 to 1 rotation. In some embodiments, the thermal sensor 104 can be turned around the portion of the longitudinal axis 94 in a range of 0.3 to 0.6 rotations. In some embodiments, however, the thermal sensor 104 may, for example, be turned or wrapped around the portion of the longitudinal axis 94 greater than 1 rotation. For example, As a result of the thermal sensor 104 being turned or wrapped around the portion of the longitudinal axis 94, the length of the thermal sensor 104 spanning the center cavity 134 is longer than that of some prior approaches. The increased length of the thermal sensor 104 passing through the center cavity 134 can allow for the thermal sensor 104 to flex over a greater length, thus reducing stress points where, for example, the thermal sensor 104 exits the thermocouple lumen 128 of the proximal stem 108 and enters the center cavity 134 and/or where the thermal sensor 104 enters the electrode pocket 122 from the center cavity 134. In an example, because the thermal sensor 104 is turned or wrapped around the portion of the longitudinal axis 94, the portion of the thermal sensor 104 in the center cavity can be compressed and can flex along the turned portion of the thermal sensor 104, as the flexible tip electrode 96 is compressed.

In addition, as a result of the thermal sensor 104 being turned or wrapped around the portion of the longitudinal axis 94, internal biasing of the flexible tip electrode 96 may be alleviated. For example, in prior approaches where the thermal sensor 104 passes through the center cavity linearly, the thermal sensor 104 may be less flexible. This can result in the flexible tip electrode 96 being deflected in a particular direction upon exertion of force upon the flexible tip electrode 96. For example, the flexible tip electrode 96 may deflect laterally when a longitudinal force is exerted on the flexible tip electrode 96. In addition, where the flexible tip electrode 96 does not have any force exerted on its tip, the linearly run thermal sensor 104 can create a biasing force that deflects the flexible tip electrode 96 in a particular direction away from a neutral position (e.g., where no biasing force is present). Embodiments of the present disclosure can provide a more flexible thermal sensor 104, which can distribute the biasing force over the turned portion of the thermal sensor. As such, when a force is exerted on the tip of the flexible tip electrode, deflection of the flexible tip electrode 96 may not be affected by the thermal sensor 104. In addition, where the flexible tip electrode 96 does not have any force exerted on its tip, the turned thermal sensor 104 can alleviate the biasing force, allowing the flexible tip electrode 96 to remain in a more neutral position.

In some embodiments, the thermal sensor 104 can be pre-formed to maintain the turn in the thermal sensor 104. In an example, the thermal sensor 104 can include an elongate thermocouple 138, such as a T-type or K-type thermocouple, for example, that can be sized and configured to be placed in a polymer (e.g., polyimide) tube 140. The polymer tube 140 can be formed using a spin formed nitinol wire, in some examples. The nitinol wire can be inserted into the polymer tube 140 and heat can be applied to the polymer tube 140 and/or the nitinol wire to introduce the turn into the polymer tube 140, as discussed herein. In some examples, air heated to 600 degrees Fahrenheit (° F.) can be blown across the polymer tube 140 that has the nitinol wire inserted within for a time period in a range of 15 to 30 seconds.

In an example, the elongate thermocouple 138 can be formed of 120 American Wire Gauge (AWG) wire and can be inserted into a proximal end of the polymer tube 140 such that the elongate thermocouple 138 extends approximately 2 inches from a distal end of the polymer tube 140. The exposed end of the elongate thermocouple 138 can be submerged into a pool of adhesive (e.g., M11 adhesive) and the distal end of the elongate thermocouple 138 can be drawn back within the polymer tube 140 until a solder joint at the distal end of the elongate thermocouple 138 is positioned within the polymer tube 140 (e.g., at a distal end of the polymer tube 140). In some embodiments, the elongate thermocouple 138 can be inserted into the polymer tube 140, such that the solder joint is positioned within the polymer tube 140 and a syringe can be used to inject the adhesive into the polymer tube 140. By injecting the adhesive into the polymer tube 140, any air bubbles that remain in the adhesive within the polymer tube can be forced out of the polymer tube 140. In some embodiments, upon introducing the adhesive into the space between the elongate thermocouple 138 and the polymer tube 140, the thermal sensor 104 can be placed in an oven to cure the adhesive at a temperature in a range of 135 to 150° F. for a time in a range of 15 to 20 minutes, in an example.

In some embodiments, the thermal sensor 104 can be positioned in the catheter tip assembly 92, such that the thermal sensor 104 passes through the thermocouple lumen 48, through the center cavity 134, and into the electrode pocket 122. In an example, where the thermal sensor 104 includes an elongate thermocouple 138, the temperature sensing component of the elongate thermocouple 138 can be inserted into the electrode pocket 122 formed in the distal face of the electrode cap 90. For instance, the temperature sensing component of the elongate thermocouple 138 can include a distal end of the elongate thermocouple 138 that has had its wire coating stripped. The stripped portion of the elongate thermocouple 138 (e.g., temperature sensing component) can be adhered within the electrode pocket 122, such that the stripped portion of the elongate thermocouple 138 is located within the electrode pocket 122 and the un-stripped portion of the elongate thermocouple 138 is located in the center cavity within the polymer tube 140.

The distal end of the thermal sensor 104 can be at an angle θ with respect to the longitudinal axis 94 formed by the catheter tip assembly. θ can be in a range of 0 degrees to 30 degrees, in some examples. Allowing for an angle θ to exist between the distal end of the thermal sensor 104 and the horizontal axis 94 can reduce an amount of bend in the distal end of the thermal sensor 104, in turn reducing an amount of stress placed on the thermal sensor at the interface between the center cavity 134 and the electrode cap 90.

Adhesive can be introduced into the electrode pocket 122 such that the adhesive completely and/or partially fills the electrode pocket 122, thus adhering the polymer tube 140 and the distal end of the thermal sensor 104 in the electrode pocket 122. In addition, adhesive can be introduced into the thermocouple lumen 128 to secure the thermal sensor 104 in the thermocouple lumen 48. In an example, the adhesives introduced into the electrode pocket 122 and the thermocouple lumen 128 can have a durometer that allows for flex of the distal end of the thermal sensor 104 within the electrode pocket 122. For instance, the adhesive can have a durometer such as that associated with an M11 adhesive, commercially available from Loctite®. Upon application of the adhesives within the electrode pocket 122 and the thermocouple lumen 48, the adhesive can be cured by heating the adhesive at a temperature in a range of 135 to 150° F., in an example. Alternatively, in some examples, the adhesive can be cured at room temperature.

In some embodiments the proximal stem 108 can comprise an inner surface 144 and a ledge feature 150. The inner surface 144 of the proximal stem 108 can define a manifold lumen through which the manifold assembly 102 can extend. The ledge feature 150 may be an annular or partially annular lip or protrusion from inner surface 144 that is sized and configured to interact with the manifold assembly 102, such that the manifold assembly 102 can be inserted a predetermined distance into the center cavity 134. The ledge feature 150 can comprise a ridge or narrowing of the inner surface 144 of the proximal stem 108. In some embodiments, the ledge feature 150 can comprise a non-continuous feature to restrict the movement of a stop tube 146, which is adhered to the manifold assembly via adhesive 148, past a certain point in the proximal stem 108 of the catheter tip assembly 92. The fluid lumen manifold 102 can include irrigation ports 142, for the passing of irrigation fluid into the center cavity and through irrigation ports 120 and/or linear gap 114, in an example.

In some embodiments, the thermal sensor 104 can be turned or wrapped around a portion of the fluid lumen manifold 102 that extends into the center cavity 134. Such a turned thermal sensor may define a three-dimensional shape that may include a helical or spiral type shape, such as that shown in the figures. In an example, the thermal sensor 104 can be turned or wrapped around a diameter that is between an outer diameter of the fluid lumen manifold 102 and an inner diameter of the electrode wall 112, which can increase an amount of slack in the thermal sensor 104, thus reducing stress points where the thermal sensor 104 is adhered to the electrode cap 90 and the proximal stem 108.

In some embodiments, the catheter tip assembly 92 can include a coil 136 that extends between the distal end of the proximal stem 108 and the proximal end of the electrode cap 90 and can encircle the thermal sensor 104 and/or the fluid lumen manifold. The coil 136 can be sized and configured such that the coil 136 can be located within the center cavity 134 of the flexible tip electrode 96. The coil can provide structural integrity to the flexible tip electrode and bias the flexible tip electrode 96 into pre-determined arrangements. The coil 136 can bias the flexible tip electrode 96 in a longitudinal direction or in a pre-bent configuration. In one embodiment, the coil 136 can comprise a resilient material such as stainless steel and/or a shape memory material such as nitinol. When flexible tip electrode 96 is at a free length that is unaffected by any force applied to the flexible tip electrode 96, the coil 136 can be partially compressed, in some examples. The partially compressed coil 136 can provide the catheter tip assembly 92 with a return to straight functionality. For example, if a longitudinal and/or lateral force are applied to flexible tip electrode 96, deflecting the electrode wall 112 and/or electrode cap 90 from an initial state, upon removal of the force, the coil 136 will return to its partially compressed state and thus return the electrode wall 112 and/or electrode cap 90 to its initial state.

In some embodiments, changing the path of the thermal sensor 104 in the center cavity from a linear configuration to a configuration where the thermal sensor 104 is turned about the linear axis 94 can result in a change in force that is necessary to compress and/or deflect the flexible tip electrode from an initial orientation. In an example, because more slack is present in the thermal sensor 104 in the turned configuration, the thermal sensor 104 may deform more easily than a thermal sensor in the linear configuration. As such, the coil can have an increased spring force versus a coil used with a thermal sensor 104 in the linear configuration. In some examples, the coil can have a spring force at approximately 0.13 of its compressed length in a range of 15 to 100 grams, although examples are not so limited.

FIG. 7A illustrates a side view of the thermal sensor shown in FIG. 6, in accordance with embodiments of the present disclosure. In an example, as discussed herein, the thermal sensor 104 can include an elongate thermocouple 138 adhered within a polymer tube 140. The elongate thermocouple 138 can include thermocouple wires 152-1, 152-2, which can be coated by wire coating 154. As discussed herein, the elongate thermocouple 138 can be adhered within the polymer tube 140 using an adhesive 156. In an example, a solder joint located at the distal end of the elongate thermocouple 138 can be inserted into the electrode pocket 122, as discussed herein, to monitor the operating temperature of the flexible tip electrode 96 and/or the temperature of tissue adjacent the flexible tip electrode 96. In some embodiments, the elongate thermocouple 138 can be stripped of the wire coating 154 distally in relation to line A'-A', which can represent an interface between the center cavity 134 and the proximal side of the electrode cap 90 (as shown in FIG. 6). Stripping the wire coating can result in an increased heat transfer between the flexible tip electrode 96 and the solder joint at the distal end of the elongate thermocouple 138 and/or between the tissue adjacent the flexible tip electrode 96 and the solder joint at the distal end of the elongate thermocouple 138, which can provide a more accurate measurement of temperature via the elongate thermocouple 138.

FIG. 7B illustrates a cross-sectional view of the thermal sensor seen in FIG. 7A taken in the direction of line 7B-7B, in accordance with embodiments of the present disclosure. As discussed herein, the thermal sensor 104 can include the elongate thermocouple 138 adhered within the polymer tube 140 with adhesive 156. From the top view, the thermocouple wire 152-2 can be seen and is coated by wire coating 154. In some embodiments, the elongate thermocouple 138 can be stripped of the wire coating 154 distally in relation to line A'-A', which can represent an interface between the center cavity 134 and the proximal side of the electrode cap 90.

FIG. 7C illustrates an end view of the thermal sensor adhered within the polymer tube seen in FIG. 7A, in accordance with embodiments of the present disclosure. The thermal sensor 104 can include an elongate thermocouple 138 that includes the thermocouple wires 152-1, 152-2 and the wire coating 154. The elongate thermocouple 138 can be adhered within polymer tube 140 with adhesive 156, which can be, for example, a two-part epoxy. In some examples, spacers can be inserted and/or built into the polymer tube 140 and/or can be placed around the elongate thermocouple 138 prior to inserting the elongate thermocouple 138 into the polymer tube 140. The spacers can center the elongate thermocouple 138 and/or a distal end and/or solder joint at the distal end of the elongate thermocouple 138, which can help in collecting a uniform temperature reading.

Figure 8A:
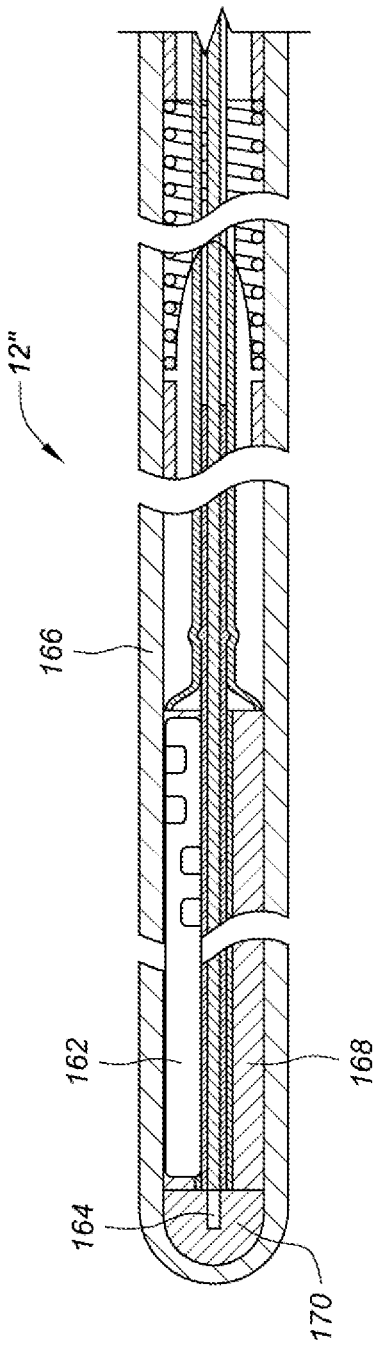
FIG. 8A depicts a cross-sectional side view of a distal portion of a guidewire with an active magnetic position sensor, in accordance with embodiments of the present disclosure.
Figure 8B:
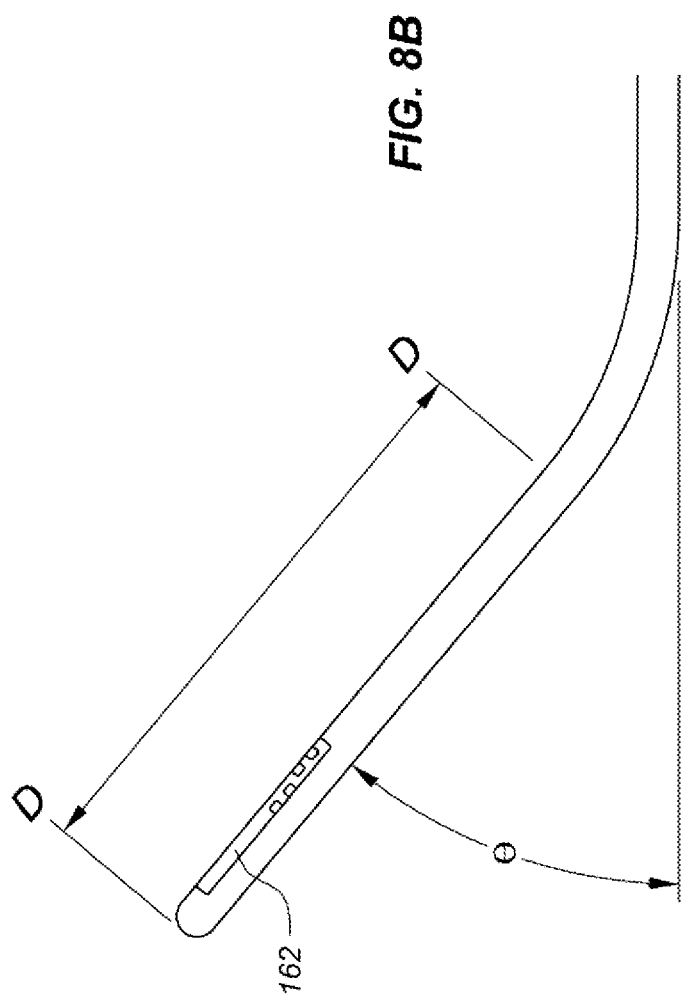
FIG. 8B depicts a diagrammatic side view an active magnetic position sensor for use with a guidewire, in accordance with embodiments of the present disclosure.

FIG. 8A depicts a cross-sectional side view of a distal portion of a guidewire 12" with an active magnetic position sensor 162, in accordance with embodiments of the present disclosure. The guidewire 12" can be a deflectable guidewire, in some embodiments, as depicted in FIG. 8B. As such, the guidewire 12" can include a core wire 164, in some embodiments. The guidewire 12" can have an outer coating 166 that surrounds the contents of the guidewire 12". In an example, the core wire 164 can extend through a center of the guidewire 12" from a proximal end to a distal end of the guidewire 12". In some prior approaches, an magnetic coil 168 can be disposed within a distal end of the guidewire 12". For example, the core wire 164 can extend through a center of the magnetic coil 78, in some embodiments. For illustrative purposes, the magnetic coil 168 is shown disposed in the distal end of the guidewire 12". In some embodiments of the present disclosure, the magnetic coil 168 is not needed, as the active magnetic position sensor 162 can be used to detect the P&O of the catheter 12'.

In some embodiments, as discussed herein, the active magnetic position sensor 162 can be smaller than a traditional magnetic coil (e.g., passive magnetic position sensor). For example, the active magnetic position sensor 162 can have a length that is approximately half that of a traditional coil, as depicted in FIG. 8B. For example, a traditional magnetic coil can have a length defined by the line DD, which can be in a range from 0.2 to 0.28 inches. A length of a traditional magnetic coil, including interconnects for connecting the coil, can be longer than desired. A longer than desired length of the magnetic coil can affect a flexibility and/or deflection of a catheter shaft in which the coil is included. In addition, the longer than desired length of the magnetic coil can occupy real estate in the distal end of the guidewire, which could be used for other components. Further, the active magnetic position sensor 162 can be cheaper to produce and install than a traditional magnetic coil.

As depicted in FIG. 8A, the active magnetic position sensor 162 can be disposed in a distal end of the guidewire 12" and proximally with respect to a distal tip 170 of the guidewire. The active magnetic position sensor 162 can be the same as and can include the same features as the active magnetic position sensor 32, as discussed in relation to FIGS. 2A and 2B. In some embodiments, the active magnetic position sensor 162 can be disposed within the guidewire 12", which has a smaller outer diameter than the catheter 12'. Thus, in some embodiments, the active magnetic position sensor 162 can have a diameter that is smaller than the active magnetic position sensor 32 placed in the catheter 12'. For example, space in the catheter 12' can limit an outer diameter of the active magnetic position sensor 32 to 0.015 inches, in some embodiments. However, space within the guidewire 12" can limit an outer diameter of the active magnetic position sensor 162 to 0.0038 inches. As such, the active magnetic position sensor 162 can have an outer diameter that is less than 0.0038 inches, in some embodiments. For example, the magnetic position sensor 162 can have an outer diameter in a range from 0.001 to 0.0038, in some embodiments.

In some embodiments, the active magnetic position sensor 162 can be positioned between the core wire 164 and the outer coating 166. An elongate axis of the active magnetic position sensor 162 can be parallel with a longitudinal axis of the guidewire 12", in some embodiments. Alternatively, the elongate axis of the active magnetic position sensor 162 can be divergent with the longitudinal axis of the guidewire 12", in some embodiments.

FIG. 8B depicts a diagrammatic side view of an active magnetic position sensor 162 for use with a guidewire 12", in accordance with embodiments of the present disclosure. As depicted in FIG. 8B, the active magnetic position sensor 162 can be disposed in a distal portion of the guidewire 12". As depicted in FIG. 8B, the active magnetic position sensor 162 can be less than one-half of a length of a traditional magnetic coil. This can allow for space savings in the guidewire and less interference with a deflectable portion of the guidewire 12", for example.

In some embodiments, the active magnetic position sensor 162 can operate based on Hall Effect physics for detection of the magnetic field. However, the active magnetic position sensor 162 can operate off of other principles for the detection of the magnetic field, as discussed herein. In some embodiments, the active magnetic position sensor 162 can be a microelectricalmechanical (MEM) sensor.

When traditional magnetic coils are used as magnetic position sensors, the coil can be connected to interconnects (e.g., wire leads) via soldering. This process can be time and cost intensive and may require a person to manually solder the coil and the interconnects together. Embodiments of the present disclosure can provide an active magnetic position sensor 162 that can be mounted to a printed circuit board via surface mount technology, which can be automated. Thus, a cost of the active magnetic position sensor 162 and installation of the active magnetic position sensor 162 can be reduced.

FIG. 8B depicts the distal tip of the guidewire 12" as being deflected by a particular angle θ, which is depicted as 35 to 45 degrees. In prior approaches that use a traditional magnetic coil, deflection of the distal portion of the guidewire 12" may be limited to a deflection in a range from 35 to 45 degrees, as a result of the magnetic coil being positioned in the distal portion. However, use of the active magnetic position sensor 162 may enable a more distal portion of the guidewire 12" to be deflected because of a shorter length that can be associated with the active magnetic position sensor 162 and/or enable the guidewire 12" to deflect by a greater angle θ. For example, the guidewire 12" can be deflected by 75 degrees when the active magnetic position sensor 162 is used instead of a traditional magnetic coil. This can improve a performance of the guidewire 12", by allowing for an increased length of the guidewire 12" to be deflected over that associated with a guidewire that utilizes a traditional magnetic coil.

Figure 8C:
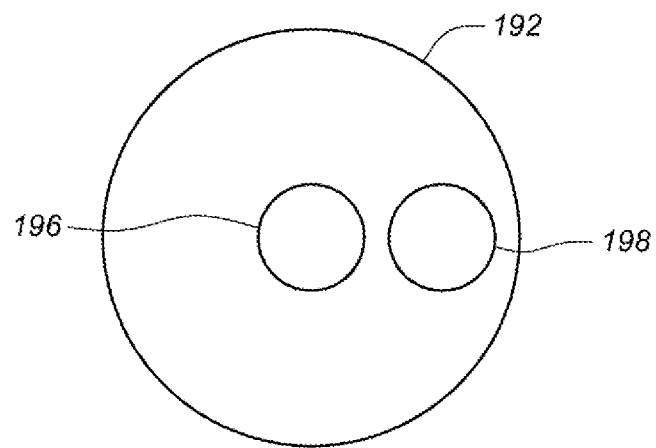
FIG. 8C depicts a proximal end view of a sensor mounting plug, in accordance with embodiments of the present disclosure.
Figure 8D:
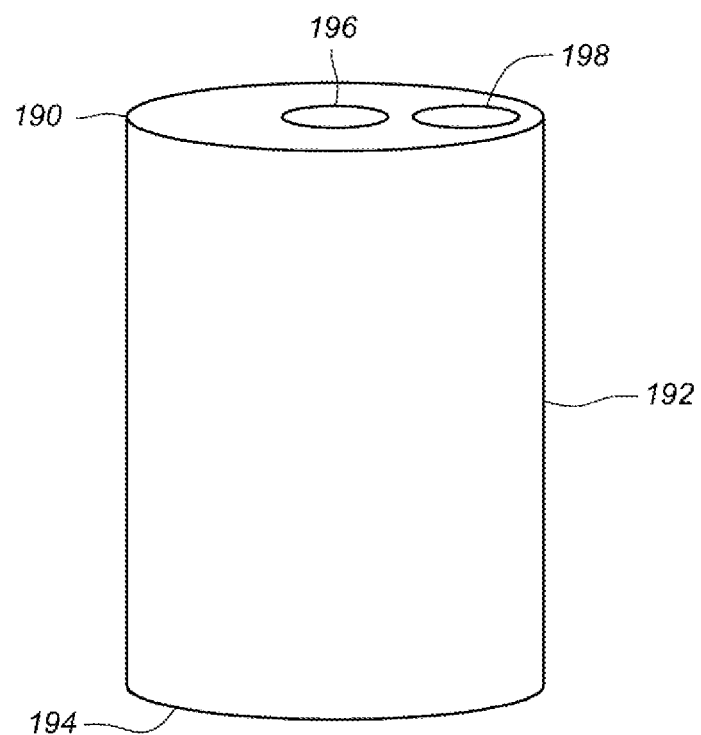
FIG. 8D depicts an isometric side and proximal end view of the sensor mounting plug, in accordance with embodiments of the present disclosure.

FIG. 8C depicts a proximal end 190 view of a sensor mounting plug 192, in accordance with embodiments of the present disclosure. FIG. 8D depicts an isometric side and proximal end 190 view of the sensor mounting plug 192, in accordance with embodiments of the present disclosure. As depicted, the sensor mounting plug 192 can include a proximal end 190 and a distal end 194 and can extend along a longitudinal axis. In some embodiments, the sensor mounting plug 192 can define a central lumen 196 through which various components can pass. The central lumen 196 can extend through a center of the sensor mounting plug 192 along a longitudinal axis defined by the sensor mounting plug 192. Although the central lumen 196 is depicted as extending through the center of the sensor mounting plug 192, the central lumen 196 can be offset from the center of the sensor mounting plug 192, in some embodiments, to house a pull wire. In some embodiments, the sensor mounting plug 192 can define a sensor mounting lumen 198, in which an active magnetic position sensor 162 can be inserted. The sensor mounting lumen 198 can extend through the sensor mounting plug 192 and can be offset from the center of the sensor mounting plug 192 (e.g., located to the side of the central lumen 196). In some embodiments, the sensor mounting lumen 198 can extend through the entire longitudinal length of the sensor mounting plug 192 (e.g., a thru hole) or can extend through a portion of the longitudinal length of the sensor mounting plug 192 (e.g., a blind hole).

In some embodiments, the outer coating 166 can be in contact and connected with the outer circumferential surface of the sensor mounting plug 192, which can help to fix the sensor mounting plug 192 in relation to the guidewire 12". In some embodiments, the longitudinal axis of the sensor mounting plug 192 can be aligned with the longitudinal axis of the guidewire 12". In some embodiments, the sensor mounting plug 192 can be connected with the distal tip 170 and/or the sensor mounting plug 192 and the distal tip 170 can be formed as a unitary piece with a sensor mounting hole extending distally through a portion of the sensor mounting plug 192 from a proximal end of the sensor mounting plug 192. The sensor mounting plug 192 can be disposed proximally with respect to the distal tip 170. In some embodiments, the sensor mounting plug 192 can be disposed adjacent and proximally with respect to the distal tip 170.

In some embodiments, the sensor mounting plug 192 can be disposed in a catheter shaft, such as a catheter shaft depicted in FIGS. 2A and 2B. The sensor mounting plug 192 can include more than two lumens. For example, the sensor mounting plug 192 can include a plurality of lumens passing therethrough, in which wires or other components (e.g., an irrigation tube, core wire, pull wire, etc.) can be housed. For example, components associated with the flexible tip assembly 34 can pass through lumens included in the sensor mounting plug 192.

Figure 8E:
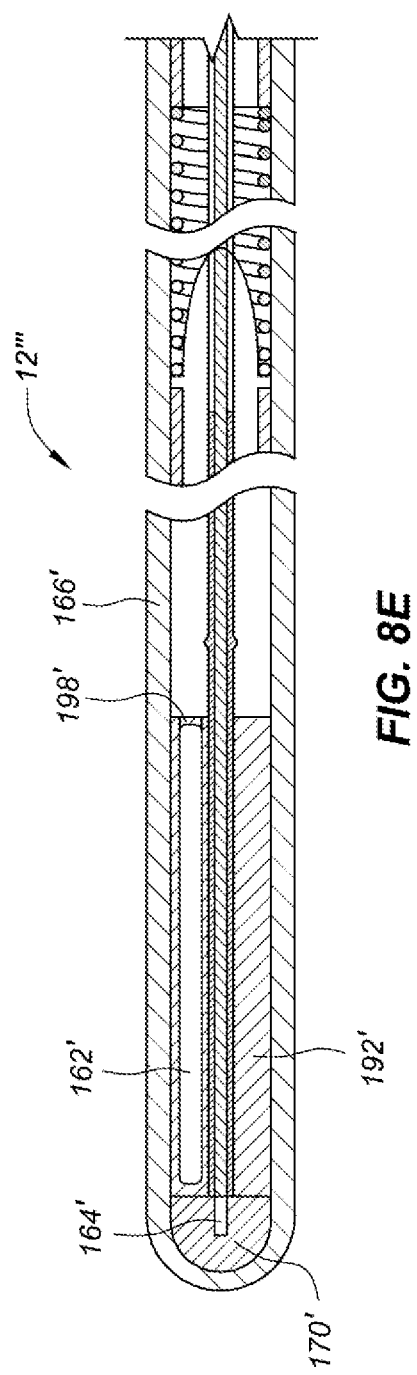
FIG. 8E depicts a cross-sectional side view of a guidewire with an active magnetic position sensor and a sensor mounting plug, in accordance with embodiments of the present disclosure.

FIG. 8E depicts a cross-sectional side view of a guidewire 12'" with an active magnetic position sensor 162' and a sensor mounting plug 192', in accordance with embodiments of the present disclosure. FIG. 8E depicts a guidewire 12'" with features similar to those discussed in relation to FIG. 8A, with the addition of the sensor mounting plug 192, but with no magnetic coil depicted. The guidewire 12'" can include a core wire 164', in some embodiments. The guidewire 12'" can have an outer coating 166' that surrounds the contents of the guidewire 12'". In an example, the core wire 164' can extend through a center of the guidewire 12' from a proximal end to a distal end of the guidewire 12'".

As depicted in FIG. 8E, the active magnetic position sensor 162' can be disposed in a distal end of the guidewire 12'" and proximally with respect to a distal tip 170' of the guidewire guidewire 12'". The active magnetic position sensor 162' can be the same as and can include the same features as the active magnetic position sensor 32, as discussed in relation to FIGS. 2A and 2B. In some embodiments, the active magnetic position sensor 162' can be disposed within the guidewire 12'", which has a smaller outer diameter than the catheter 12'. Thus, in some embodiments, the active magnetic position sensor 162' can have a diameter that is smaller than the active magnetic position sensor 32 placed in the catheter 12'. For example, space in the catheter 12' can limit an outer diameter of the active magnetic position sensor 32 to 0.015 inches, in some embodiments. However, space within the guidewire 12″ can limit an outer diameter of the active magnetic position sensor 162′ to 0.0038 inches. As such, the active magnetic position sensor 162′ can have an outer diameter that is less than 0.0038 inches, in some embodiments. For example, the magnetic position sensor 162′ can have an outer diameter in a range from 0.001 to 0.0038, in some embodiments.

In some embodiments, the active magnetic position sensor 162′ can be positioned between the core wire 164′ and the outer coating 166′. An elongate axis of the active magnetic position sensor 162′ can be parallel with a longitudinal axis of the guidewire 12‴, in some embodiments. Alternatively, the elongate axis of the active magnetic position sensor 162′ can be divergent with the longitudinal axis of the guidewire 12‴, in some embodiments.

The active magnetic position sensor 162′ can be housed in a sensor mounting lumen 198′ defined by the sensor mounting plug 192′. As depicted, the sensor mounting plug 192′ can extend along a longitudinal axis. In some embodiments, the sensor mounting plug 192′ can define a central lumen through which various components can pass (e.g., central lumen 196), which in some embodiments can extend along a longitudinal axis defined by the sensor mounting plug 192′ and through the center of the sensor mounting plug 192′ and/or can be offset from the center of the sensor mounting plug 192′. In some embodiments, the sensor mounting plug 192′ can define a sensor mounting lumen 198′, in which the active magnetic position sensor 162′ can be inserted. The sensor mounting lumen 198′ can extend through the sensor mounting plug 192′ and can be offset from a central longitudinal axis of the sensor mounting plug 192′. Due to a limited space which can be present in catheters and/or guidewires, the lumens defined by the sensor mounting plug 192′ can be connected (e.g., form a slot). For example, with reference to FIGS. 8C and 8D, an inner wall is depicted between the central lumen 196 and the sensor mounting lumen 198 and an outer wall is depicted between the sensor mounting lumen 198 and an outer surface of the sensor mounting plug 192. In contrast, FIG. 8E depicts no wall between the central lumen and the sensor mounting lumen 198′ and no wall between the sensor mounting lumen 198′ and an outer surface of the sensor mounting plug 192′, effectively forming a slot in which the active position sensor 162′ is disposed. In some embodiments, more space can be available in a catheter than a guidewire and thus the sensor mounting lumen 198′ and various other lumens defined by the sensor mounting plug 192′ can remain as separate lumens with walls disposed between them. In some embodiments, the sensor mounting lumen 198′ can extend through the entire longitudinal length of the sensor mounting plug 192′ (e.g., a thru hole) or can extend through a portion of the longitudinal length of the sensor mounting plug 192′ (e.g., a blind hole).

In some embodiments, the outer coating 166′ can be in contact and connected with the outer circumferential surface of the sensor mounting plug 192′, which can help to fix the sensor mounting plug 192′ in relation to the guidewire 12′. In some embodiments, the longitudinal axis of the sensor mounting plug 192′ can be aligned with the longitudinal axis of the guidewire 12‴. In some embodiments, the sensor mounting plug 192′ can be connected with the distal tip 170′ and/or the sensor mounting plug 192′ and the distal tip 170′ can be formed as a unitary piece with a sensor mounting hole extending distally through a portion of the sensor mounting plug 192′ from a proximal end of the sensor mounting plug 192′. The sensor mounting plug 192′ can be disposed proximally with respect to the distal tip 170′. In some embodiments, the sensor mounting plug 192′ can be disposed adjacent and proximally with respect to the distal tip 170′.

In some embodiments, the sensor mounting plug 192′ can be disposed in a catheter shaft, such as a catheter shaft depicted in FIGS. 2A and 2B. The sensor mounting plug 192′ can include more than two lumens. For example, the sensor mounting plug 192′ can include a plurality of lumens passing therethrough, in which wires or other components (e.g., an irrigation tube, core wire, pull wire, etc.) can be housed. For example, components associated with the flexible tip assembly 34 can pass through lumens included in the sensor mounting plug 192′.

Figure 9:
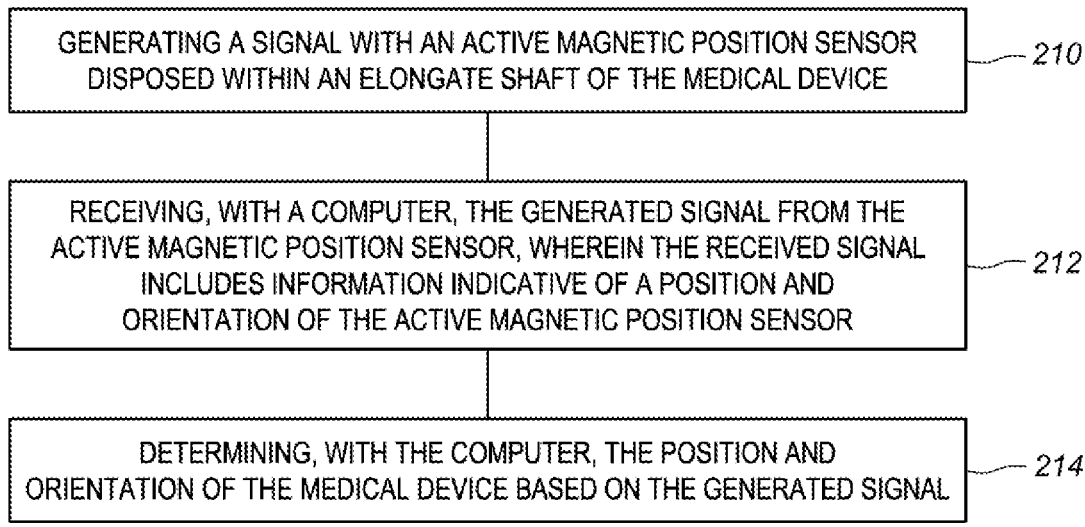
FIG. 9 depicts a method flow diagram for determining a position and orientation of a medical device, in accordance with embodiments of the present disclosure.

FIG. 9 depicts a method flow diagram for determining a P&O of a medical device, in accordance with embodiments of the present disclosure. In some embodiments, the method can include generating a signal with an active magnetic position sensor disposed within an elongate shaft of the medical device, at method flow box 210. The active magnetic position sensor can generate the signal in response to being disposed in a magnetic field, which can be generated by a magnetic field generator. In some embodiments, the magnetic field generator can be in communication with the magnetic positioning system.

The method can include, at method flow box 212, receiving, with a computer, the generated signal from the active magnetic position sensor, wherein the received signal includes information indicative of a P&O of the active magnetic position sensor. In some embodiments, the computer can be in communication with or part of the magnetic positioning system. The signal can be received with a magnetic positioning system, as previously discussed herein. The active magnetic position sensor can be provided power, in contrast to a traditional magnetic coil sensor, which is a passive type of sensor, requiring no power. Power can be supplied to the active magnetic position sensor via a power generating integrated circuit, which is electrically coupled to the active magnetic position sensor. In some embodiments, power can be supplied to the active magnetic position sensor via the magnetic positioning system, which is electrically coupled to the active magnetic position sensor. Providing power to the active magnetic position sensor enables the active magnetic position sensor to produce a signal that is indicative of a particular P&O in the magnetic field.

In some embodiments, the method can include determining, with the computer, the P&O of the medical device based on the generated signal, at method flow box 214. In an example, the computer can be associated with or in communication with the magnetic positioning system and can determine the P&O of the medical device with six degrees of freedom. Although the P&O of the medical device is determined with six degrees of freedom, the P&O can be determined with fewer than six degrees of freedom (e.g., three degrees of freedom, five degrees of freedom).

Figure 10:
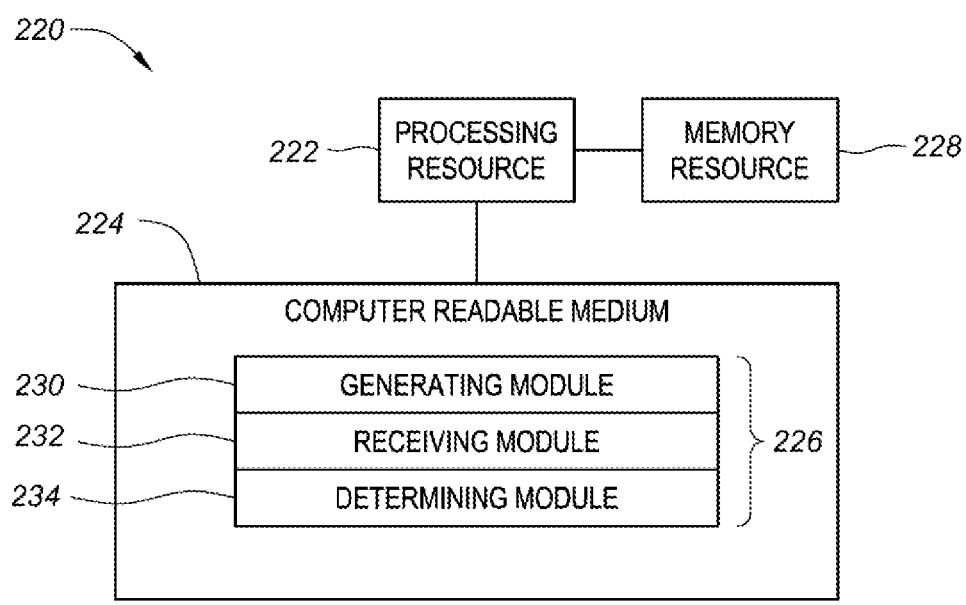
FIG. 10 illustrates a block diagram of an example of a computer-readable medium in communication with processing resources of a computing device, in accordance with embodiments of the present disclosure.

FIG. 10 illustrates a block diagram of an example of a computer-readable medium in communication with processing resources of a computing device, in accordance with embodiments of the present disclosure. The computer system 220, as discussed in relation to FIG. 1, can utilize software, hardware, firmware, and/or logic to perform a number of functions. The computer system 220 can include a number of remote computing devices.

The computer system 220 can be a combination of hardware and program instructions configured to perform a number of functions, and in some embodiments can be representative of the magnetic positioning system 14. The hardware, for example, can include one or more processing resources 222, computer readable medium (CRM) 224, etc. The program instructions (e.g., computer-readable instructions (CRI) 226) can include instructions stored on CRM 224 and executable by the processing resource 222 to implement a desired function (e.g., determine the P&O of the medical device based on the signal, etc.). The CRI 226 can also be stored in remote memory managed by a server and represent an installation package that can be downloaded, installed, and executed. The computer system 220 can include memory resources 228, and the processing resources 222 can be coupled to the memory resources 228.

Processing resources 222 can execute CRI 226 that can be stored on an internal or external non-transitory CRM 224. The processing resources 222 can execute CRI 226 to perform various functions, including the functions described with respect to FIG. 1 to FIG. 9.

A number of modules 230, 232, 234 can be sub-modules or other modules. For example, the generating module 230 and the receiving module 232 can be sub-modules and/or contained within a single module. Furthermore, the number of modules 103, 232, 234 can comprise individual modules separate and distinct from one another.

A receiving surface model module 67 can comprise CRI 66 and can be executed by the processing resource 32 to receive a surface model of the heart 10 corresponding to an end diastole phase of a cardiac cycle. The surface model of the heart 10 can be formed from location data received from the electrode 17 and can correspond to a reference cardiac phase (e.g., end diastole phase). Alternatively, the surface model of the heart 10 can be generated at a previous time and received via the computer system 20.

A generating module 230 can comprise CRI 226 and can be executed by the processing resource 222 to generate a signal with an active magnetic position sensor disposed within an elongate shaft of the medical device. As discussed herein, the active magnetic position sensor can generate the signal, which is indicative of a P&O of the active magnetic position sensor and thus the medical device. In some embodiments, the active magnetic position sensor can generate the signal in response to being placed in a magnetic field.

A receiving module 232 can comprise CRI 226 and can be executed by the processing resource 222 to receive, with a computer, the generated signal from the active magnetic position sensor, wherein the received signal includes information indicative of a P&O of the active magnetic position sensor. In some embodiments, the active magnetic position sensor can be in communication (e.g., wired or wireless) with a magnetic positioning system. The magnetic positioning system can receive the generated signal in some embodiments.

A determining module 234 can comprise CRI 226 and can be executed by the processing resource 222 to determine, with the computer, the P&O of the medical device based on the generated signal. As discussed herein, the P&O of the medical device can be determined with six degrees of freedom.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of an active magnetic position sensor has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter tip assembly, comprising:
a proximal stem that comprises a lumen;
an electrode wall that comprises a center cavity, the electrode wall coupled to a distal end of the proximal stem, and wherein the electrode wall is configured to distribute energy to a tissue;
an electrode cap coupled to a distal end of the electrode wall, the electrode cap defining an electrode pocket in a distal face of the electrode cap; and
an elongate thermocouple extending through the lumen of the proximal stem and the center cavity and into the electrode pocket defined by the electrode cap, wherein:
the elongate thermocouple is turned around a portion of a longitudinal axis defined by the catheter tip assembly,
a distal end of the elongate thermocouple is disposed in the electrode pocket at a non-zero angle with respect to the longitudinal axis defined by the catheter tip assembly,
the elongate thermocouple distributes a biasing force over the turned portion of the elongate thermocouple, and
application of a force to the electrode cap causes the electrode wall and the elongate thermocouple to flex.

2. The catheter tip assembly of claim 1, wherein the turned portion of the elongate thermocouple is turned in a helical shape around the portion of the longitudinal axis.

3. The catheter tip assembly of claim 1, wherein:
a catheter shaft is coupled to a proximal end of the proximal stem; and
the elongate thermocouple extends from the electrode cap through a lumen of the catheter shaft.

4. The catheter tip assembly of claim 1, wherein the elongate thermocouple is turned around the portion of the longitudinal axis between the distal end of the proximal stem and a proximal end of the electrode cap.

5. The catheter tip assembly of claim 1, further comprising a coil that extends between the distal end of the proximal stem and the proximal end of the electrode cap.

6. The catheter tip assembly of claim 5, wherein the coil has a spring force in a range of 15 to 100 grams.

7. The catheter tip assembly of claim 1, wherein the elongate thermocouple is adhered to the electrode cap and the proximal stem.

8. The catheter tip assembly of claim 1, wherein the elongate thermocouple is inserted within a lumen of a formed polymer tube, wherein a distal end of the formed polymer tube is located within the electrode pocket in the electrode cap.

9. The catheter tip assembly of claim 1, further comprising an active magnetic position sensor disposed in the proximal stem.

10. A catheter, comprising:
an electrode wall that comprises a center cavity, wherein the electrode wall is configured to distribute energy to a tissue;
an electrode cap coupled to a distal end of the electrode wall, the electrode cap defining an electrode pocket in a distal face of the electrode cap;
an elongate thermocouple turned around a portion of a longitudinal axis defined by the catheter; and
a fluid lumen manifold, wherein:
the elongate thermocouple is turned around the fluid lumen manifold,
the elongate thermocouple is disposed adjacent to the fluid lumen manifold in the center cavity,
the elongate thermocouple is disposed in the electrode pocket at a non-zero angle with respect to the longitudinal axis defined by the catheter tip assembly,
application of a force to the electrode cap causes the electrode wall and the elongate thermocouple disposed adjacent to the fluid lumen manifold to flex.

11. The catheter of claim 10, further comprising a proximal stem coupled to a proximal end of the electrode wall.

12. The catheter of claim 11, further comprising a catheter shaft coupled to a proximal end of the proximal stem, wherein the elongate thermocouple extends through the catheter shaft to a proximal end of the catheter shaft, and wherein an active magnetic position sensor is disposed in the catheter shaft.

13. A catheter tip assembly comprising:
an electrode wall that comprises a center cavity, wherein the electrode wall is configured to distribute energy to a tissue;
an elongate thermocouple turned around a portion of a longitudinal axis defined by the catheter tip assembly;
a fluid lumen manifold, wherein;
the elongate thermocouple is turned around the fluid lumen manifold,
a diameter at which the elongate thermocouple is turned around the fluid lumen manifold is between an outer diameter of the fluid lumen manifold and an inner diameter of the electrode wall, and
application of a force to the electrode wall causes the electrode wall and the elongate thermocouple to flex; and
an electrode cap, wherein the electrode cap comprises an electrode pocket formed in a distal face of the electrode cap, wherein a most distal end of the elongate thermocouple is disposed in the electrode pocket, at a non-zero angle with respect to the longitudinal axis of the catheter tip assembly.

14. The catheter tip assembly of claim 13, wherein the elongate thermocouple is turned around the portion of the longitudinal axis in a range from 0.2 to 1 turn.

15. The catheter tip assembly of claim 13, wherein the elongate thermocouple is turned in a spiral shape around the portion of the longitudinal axis.

16. The catheter tip assembly of claim 13, further comprising an active magnetic position sensor.

* * * * *